(12) United States Patent
Barchen et al.

(10) Patent No.: US 11,730,892 B2
(45) Date of Patent: Aug. 22, 2023

(54) PARTIAL DOOR CLOSURE PREVENTION SPRING

(71) Applicant: West Pharma. Services IL, Ltd., Ra'anana (IL)

(72) Inventors: Lior Barchen, Gani Tal (IL); Yossi Bar-El, Beit Arye (IL)

(73) Assignee: West Pharma. Services IL, Ltd., Ra'anana (IL)

( * ) Notice: Subject to any disclaimer, the term of this patent is extended or adjusted under 35 U.S.C. 154(b) by 1239 days.

(21) Appl. No.: 16/321,557

(22) PCT Filed: Dec. 21, 2016

(86) PCT No.: PCT/US2016/068049
§ 371 (c)(1),
(2) Date: Jan. 29, 2019

(87) PCT Pub. No.: WO2018/026385
PCT Pub. Date: Feb. 8, 2018

(65) Prior Publication Data
US 2019/0151562 A1    May 23, 2019

Related U.S. Application Data

(60) Provisional application No. 62/369,505, filed on Aug. 1, 2016.

(51) Int. Cl.
*A61M 5/32* (2006.01)
*A61M 5/14* (2006.01)
*E05B 65/00* (2006.01)

(52) U.S. Cl.
CPC ............ *A61M 5/3202* (2013.01); *A61M 5/14* (2013.01); *E05B 65/00* (2013.01); *A61M 2209/06* (2013.01)

(58) Field of Classification Search
CPC ............ A61M 5/3202; A61M 2209/06; A61M 11/006; A61M 15/0001; E05B 65/00
See application file for complete search history.

(56) References Cited

U.S. PATENT DOCUMENTS

| 1,795,630 | A | 3/1931 | Wilson |
| 2,860,635 | A | 11/1958 | Wilburn |

(Continued)

FOREIGN PATENT DOCUMENTS

| CN | 1224341 A | 7/1999 |
| CN | 1408443 A | 4/2003 |

(Continued)

OTHER PUBLICATIONS

Office Action dated Oct. 11, 2017 in U.S. Appl. No. 29/605,061, by Cabiri.

(Continued)

*Primary Examiner* — Sarah Al Hashimi
*Assistant Examiner* — Hans Kaliher
(74) *Attorney, Agent, or Firm* — Blank Rome LLP

(57) ABSTRACT

A drug delivery device, including: housing, wherein said housing defines an opening and a chamber for a drug cartridge; a movable door connected to the housing, having a range of movement between a fully open position and a closed position, wherein the door blocks access to said opening when the door is in said closed position; a biasing element connected to the housing or the door, wherein the biasing element is positioned to interfere with the movement of the door by applying an opening force to open the door when the range of movement of the door is near the closed position, thus defining an exclusion zone; and a locking mechanism between the door and the housing, the locking (Continued)

mechanism applies a locking force on the door greater and in an opposite direction to the force applied by the biasing element.

12 Claims, 16 Drawing Sheets

(56) References Cited

U.S. PATENT DOCUMENTS

| | | |
|---|---|---|
| 3,203,269 A | 8/1965 | Perrine |
| 3,212,685 A | 10/1965 | James et al. |
| 3,782,365 A | 1/1974 | Pinna |
| 3,794,028 A | 2/1974 | Mueller et al. |
| 3,946,732 A | 3/1976 | Hurscham |
| 3,994,295 A | 11/1976 | Wulff |
| 4,026,128 A | 5/1977 | Blanco |
| 4,167,663 A | 9/1979 | Granzow et al. |
| 4,195,636 A | 4/1980 | Behnke |
| 4,218,724 A | 8/1980 | Kaufman |
| 4,273,122 A | 6/1981 | Whitney et al. |
| 4,276,879 A * | 7/1981 | Yiournas ............... A61D 1/025 604/154 |
| 4,300,554 A | 11/1981 | Hessberg et al. |
| 4,396,385 A | 8/1983 | Kelly et al. |
| 4,403,987 A | 9/1983 | Gottinger |
| 4,435,173 A | 3/1984 | Siposs et al. |
| 4,465,478 A | 8/1984 | Sabelman et al. |
| 4,565,543 A | 1/1986 | Bekkering et al. |
| 4,585,439 A | 4/1986 | Michel |
| 4,599,082 A | 7/1986 | Grimard |
| 4,601,702 A | 7/1986 | Hudson |
| 4,634,426 A | 1/1987 | Kamen |
| 4,685,903 A | 8/1987 | Cable et al. |
| 4,689,043 A | 8/1987 | Bisha |
| 4,698,055 A | 10/1987 | Sealfon |
| 4,810,215 A | 3/1989 | Kaneko |
| 4,850,966 A | 7/1989 | Grau et al. |
| 4,867,743 A | 9/1989 | Vaillancourt |
| 4,886,499 A | 12/1989 | Cirelli et al. |
| 4,908,014 A | 3/1990 | Kroyer |
| 4,919,596 A | 4/1990 | Slate et al. |
| 4,929,241 A | 5/1990 | Kulli |
| 4,950,235 A | 8/1990 | Slate et al. |
| 4,950,246 A | 8/1990 | Muller |
| D322,671 S | 12/1991 | Szwarc |
| 5,090,877 A | 2/1992 | D'Silva |
| 5,109,850 A | 5/1992 | Blanco et al. |
| 5,112,317 A | 5/1992 | Michel |
| 5,131,816 A | 7/1992 | Brown et al. |
| 5,190,521 A | 3/1993 | Hubbard et al. |
| 5,254,096 A | 10/1993 | Rondelet et al. |
| 5,300,045 A | 4/1994 | Plassche, Jr. |
| 5,342,313 A | 8/1994 | Campbell et al. |
| 5,348,544 A | 9/1994 | Sweeney et al. |
| 5,354,287 A | 10/1994 | Wacks |
| 5,364,364 A | 11/1994 | Kasvikis et al. |
| 5,366,498 A | 11/1994 | Brannan et al. |
| 5,383,865 A | 1/1995 | Michel |
| 5,411,482 A | 5/1995 | Campbell |
| 5,445,621 A | 8/1995 | Poli et al. |
| 5,478,315 A | 12/1995 | Brothers et al. |
| 5,482,446 A | 1/1996 | Williamson et al. |
| 5,496,274 A | 3/1996 | Graves et al. |
| 5,501,665 A | 3/1996 | Jhuboo et al. |
| 5,505,709 A | 4/1996 | Funderburk et al. |
| D372,098 S | 7/1996 | Lattin et al. |
| 5,558,639 A | 9/1996 | Gangemi et al. |
| 5,562,686 A | 10/1996 | Sauer et al. |
| 5,593,390 A | 1/1997 | Castellano et al. |
| 5,616,132 A | 4/1997 | Newman |
| 5,643,218 A | 7/1997 | Lynn et al. |
| 5,645,955 A | 7/1997 | Maglica |
| 5,647,853 A | 7/1997 | Feldmann et al. |
| 5,658,133 A | 8/1997 | Anderson et al. |
| 5,662,678 A | 9/1997 | Macklin |
| 5,672,160 A | 9/1997 | Oesterlind et al. |
| D384,745 S | 10/1997 | Lattin et al. |
| 5,690,618 A | 11/1997 | Smith et al. |
| D393,314 S | 4/1998 | Meisner et al. |
| 5,766,186 A | 6/1998 | Faraz et al. |
| 5,779,676 A | 7/1998 | Kriesel et al. |
| 5,795,675 A | 8/1998 | Maglica |
| 5,800,420 A | 9/1998 | Gross et al. |
| 5,807,375 A | 9/1998 | Gross et al. |
| 5,814,020 A | 9/1998 | Gross |
| 5,820,406 A | 10/1998 | Hetherington |
| 5,830,187 A | 11/1998 | Kriesel et al. |
| 5,836,920 A | 11/1998 | Robertson |
| 5,848,991 A | 12/1998 | Gross et al. |
| 5,851,197 A | 12/1998 | Marano et al. |
| 5,858,001 A | 1/1999 | Tsals et al. |
| 5,858,008 A | 1/1999 | Capaccio |
| 5,868,710 A | 2/1999 | Battiato et al. |
| 5,931,814 A | 8/1999 | Alex et al. |
| 5,941,850 A | 8/1999 | Shah et al. |
| 5,948,392 A | 9/1999 | Haslwanter et al. |
| 5,954,697 A | 9/1999 | Srisathapat et al. |
| 5,957,895 A | 9/1999 | Sage et al. |
| 5,968,011 A | 10/1999 | Larsen et al. |
| 5,993,423 A | 11/1999 | Choi |
| 5,997,501 A | 12/1999 | Gross et al. |
| 6,004,297 A | 12/1999 | Steenfeldt-Jensen et al. |
| 6,033,245 A | 3/2000 | Yamkovoy |
| 6,033,377 A | 3/2000 | Rasmussen et al. |
| 6,064,797 A | 5/2000 | Crittendon et al. |
| 6,074,369 A | 6/2000 | Sage et al. |
| 6,117,575 A | 9/2000 | Dinsdale |
| 6,138,865 A * | 10/2000 | Gilmore ............... A61J 7/0481 221/7 |
| 6,149,614 A | 11/2000 | Dunshee et al. |
| 6,160,487 A | 12/2000 | DeLuca |
| 6,175,688 B1 | 1/2001 | Cassidy et al. |
| 6,186,982 B1 | 2/2001 | Gross et al. |
| 6,200,289 B1 | 3/2001 | Hochman et al. |
| 6,200,296 B1 | 3/2001 | Dibiasi et al. |
| 6,224,569 B1 | 5/2001 | Brimhall |
| 6,248,093 B1 | 6/2001 | Moberg |
| 6,277,095 B1 | 8/2001 | Kriesel et al. |
| 6,277,098 B1 | 8/2001 | Klitmose et al. |
| 6,277,099 B1 | 8/2001 | Strowe et al. |
| 6,287,283 B1 | 9/2001 | Ljunggreen et al. |
| 6,293,925 B1 | 9/2001 | Safabash et al. |
| 6,302,633 B1 | 10/2001 | Poe |
| 6,305,908 B1 | 10/2001 | Hermann et al. |
| 6,336,729 B1 | 1/2002 | Pavelle et al. |
| 6,345,968 B1 | 2/2002 | Shupe |
| 6,362,591 B1 | 3/2002 | Moberg |
| 6,377,848 B1 | 4/2002 | Garde et al. |
| 6,391,005 B1 | 5/2002 | Lum et al. |
| 6,423,029 B1 | 7/2002 | Elsberry |
| 6,423,035 B1 | 7/2002 | Das et al. |
| 6,423,036 B1 | 7/2002 | Van Huizen |
| D465,026 S | 10/2002 | May et al. |
| 6,458,102 B1 | 10/2002 | Mann et al. |
| 6,485,461 B1 | 11/2002 | Mason et al. |
| 6,485,465 B2 | 11/2002 | Moberg et al. |
| 6,500,150 B1 | 12/2002 | Gross et al. |
| 6,503,231 B1 | 1/2003 | Prausnitz et al. |
| 6,511,336 B1 | 1/2003 | Turek et al. |
| 6,517,517 B1 | 2/2003 | Farrugia et al. |
| D471,274 S | 3/2003 | Diaz et al. |
| D471,983 S | 3/2003 | Hippolyte et al. |
| 6,530,901 B1 | 3/2003 | Tsukada et al. |
| 6,555,986 B2 | 4/2003 | Moberg |
| 6,558,351 B1 | 5/2003 | Steil et al. |
| 6,589,229 B1 | 7/2003 | Connelly et al. |
| 6,595,205 B2 * | 7/2003 | Andersson ......... A61M 15/0091 128/200.23 |
| 6,595,956 B1 | 7/2003 | Gross et al. |
| 6,595,960 B2 | 7/2003 | West et al. |
| 6,599,272 B1 | 7/2003 | Hjerlman et al. |
| 6,632,201 B1 | 10/2003 | Mathias et al. |
| 6,645,181 B1 | 11/2003 | Lavi et al. |

(56) References Cited

U.S. PATENT DOCUMENTS

| | | |
|---|---|---|
| 6,652,482 B2 | 11/2003 | Hochman |
| 6,656,158 B2 | 12/2003 | Mahoney et al. |
| 6,656,159 B2 | 12/2003 | Flaherty |
| 6,659,980 B2 | 12/2003 | Moberg et al. |
| 6,673,033 B1 | 1/2004 | Sciulli et al. |
| 6,679,862 B2 | 1/2004 | Diaz et al. |
| 6,689,118 B2 | 2/2004 | Alchas et al. |
| 6,699,218 B2 | 3/2004 | Flaherty et al. |
| 6,722,916 B2 | 4/2004 | Buccinna et al. |
| 6,743,211 B1 | 6/2004 | Prausnitz et al. |
| 6,749,587 B2 | 6/2004 | Flaherty |
| 6,752,787 B1 | 6/2004 | Causey et al. |
| 6,768,425 B2 | 7/2004 | Flaherty et al. |
| 6,786,890 B2 | 9/2004 | Preuthun et al. |
| 6,800,071 B1 | 10/2004 | Mcconnell et al. |
| 6,805,687 B2 | 10/2004 | Dextradeur et al. |
| 6,824,529 B2 | 11/2004 | Gross et al. |
| 6,843,782 B2 | 1/2005 | Gross et al. |
| 6,854,620 B2 | 2/2005 | Ramey |
| 6,905,298 B1 | 6/2005 | Haring |
| 6,908,452 B2 | 6/2005 | Diaz et al. |
| 6,950,028 B2 | 9/2005 | Zweig |
| 6,960,192 B1 | 11/2005 | Flaherty et al. |
| 6,972,002 B2 | 12/2005 | Thorne |
| 6,997,727 B1 | 2/2006 | Legrady et al. |
| 7,001,360 B2 | 2/2006 | Veasey et al. |
| 7,034,223 B2 | 4/2006 | Fan et al. |
| 7,048,715 B2 | 5/2006 | Diaz et al. |
| 7,060,054 B2 | 6/2006 | Nissels |
| 7,060,059 B2 | 6/2006 | Keith et al. |
| 7,097,637 B2 | 8/2006 | Triplett et al. |
| 7,128,727 B2 | 10/2006 | Flaherty et al. |
| 7,144,384 B2 | 12/2006 | Gorman et al. |
| 7,193,521 B2 | 3/2007 | Moberg et al. |
| D544,092 S | 6/2007 | Lewis |
| 7,225,694 B2 | 6/2007 | Said |
| 7,247,149 B2 | 7/2007 | Beyerlein |
| 7,250,037 B2 | 7/2007 | Shermer et al. |
| 7,267,669 B2 | 9/2007 | Staunton et al. |
| 7,291,132 B2 | 11/2007 | Deruntz et al. |
| 7,291,159 B2 | 11/2007 | Schmelzeisen-Redeker et al. |
| 7,303,549 B2 | 12/2007 | Flaherty et al. |
| 7,344,385 B2 | 3/2008 | Chen |
| 7,364,570 B2 | 4/2008 | Gerondale et al. |
| 7,390,314 B2 | 6/2008 | Stutz et al. |
| 7,407,493 B2 | 8/2008 | Cane |
| D578,210 S | 10/2008 | Muta et al. |
| 7,455,663 B2 | 11/2008 | Bikovsky |
| 7,465,290 B2 | 12/2008 | Reilly |
| 7,488,181 B2 | 2/2009 | Van |
| 7,497,842 B2 | 3/2009 | Diaz et al. |
| 7,501,587 B2 | 3/2009 | English |
| 7,503,786 B2 | 3/2009 | Kato et al. |
| 7,524,304 B2 | 4/2009 | Genosar |
| 7,530,964 B2 | 5/2009 | Lavi et al. |
| 7,547,281 B2 | 6/2009 | Hayes et al. |
| 7,563,253 B2 | 7/2009 | Tanner et al. |
| 7,565,208 B2 | 7/2009 | Harris et al. |
| 7,569,050 B2 | 8/2009 | Moberg et al. |
| D600,341 S | 9/2009 | Loerwald |
| 7,585,287 B2 | 9/2009 | Bresina et al. |
| 7,588,559 B2 | 9/2009 | Aravena et al. |
| 7,589,974 B2 | 9/2009 | Grady et al. |
| D602,155 S | 10/2009 | Foley et al. |
| D602,586 S | 10/2009 | Foley et al. |
| D604,835 S | 11/2009 | Conley |
| 7,621,893 B2 | 11/2009 | Moberg et al. |
| 7,628,770 B2 | 12/2009 | Ethelfeld |
| 7,628,772 B2 | 12/2009 | Mcconnell et al. |
| 7,628,782 B2 | 12/2009 | Mair et al. |
| 7,637,891 B2 | 12/2009 | Wall |
| 7,637,899 B2 | 12/2009 | Woolston et al. |
| 7,641,649 B2 | 1/2010 | Moberg et al. |
| 7,660,627 B2 | 2/2010 | Mcnichols et al. |
| 7,678,079 B2 | 3/2010 | Shermer et al. |
| 7,682,338 B2 | 3/2010 | Griffin |
| 7,686,787 B2 | 3/2010 | Moberg et al. |
| 7,699,829 B2 | 4/2010 | Harris et al. |
| 7,699,833 B2 | 4/2010 | Moberg et al. |
| 7,704,088 B2 | 4/2010 | Sakamoto |
| 7,704,227 B2 | 4/2010 | Moberg et al. |
| 7,704,229 B2 | 4/2010 | Moberg et al. |
| 7,704,231 B2 | 4/2010 | Pongpairochana et al. |
| 7,708,717 B2 | 5/2010 | Estes et al. |
| 7,713,238 B2 | 5/2010 | Mernoe |
| 7,713,240 B2 | 5/2010 | Istoc et al. |
| 7,717,913 B2 | 5/2010 | Novak et al. |
| 7,722,574 B2 | 5/2010 | Toman et al. |
| 7,736,344 B2 | 6/2010 | Moberg et al. |
| 7,744,589 B2 | 6/2010 | Mounce et al. |
| 7,749,194 B2 | 7/2010 | Edwards et al. |
| 7,753,879 B2 | 7/2010 | Mernoe |
| 7,766,873 B2 | 8/2010 | Moberg et al. |
| 7,776,030 B2 | 8/2010 | Estes et al. |
| 7,780,636 B2 | 8/2010 | Radmer et al. |
| 7,780,637 B2 | 8/2010 | Jerde et al. |
| 7,789,857 B2 | 9/2010 | Moberg et al. |
| 7,789,862 B2 | 9/2010 | Thorne, Jr. |
| 7,801,599 B2 | 9/2010 | Young et al. |
| 7,806,868 B2 | 10/2010 | De Polo et al. |
| 7,815,622 B2 | 10/2010 | Istoc et al. |
| 7,828,528 B2 | 11/2010 | Estes et al. |
| 7,837,659 B2 | 11/2010 | Bush et al. |
| 7,846,132 B2 | 12/2010 | Gravesen et al. |
| 7,854,723 B2 | 12/2010 | Hwang et al. |
| 7,857,131 B2 | 12/2010 | Vedrine |
| 7,879,025 B2 | 2/2011 | Jacobson et al. |
| 7,879,026 B2 | 2/2011 | Estes et al. |
| 7,892,206 B2 | 2/2011 | Moberg et al. |
| 7,918,825 B2 | 4/2011 | O'Connor et al. |
| 7,918,843 B2 | 4/2011 | Genosar et al. |
| 7,935,104 B2 | 5/2011 | Yodat et al. |
| 7,935,105 B2 | 5/2011 | Miller et al. |
| 7,938,803 B2 | 5/2011 | Mernoe et al. |
| 7,955,305 B2 | 6/2011 | Moberg et al. |
| 7,967,784 B2 | 6/2011 | Pongpairochana et al. |
| 7,967,795 B1 | 6/2011 | Cabiri |
| 7,981,105 B2 | 7/2011 | Adair et al. |
| 7,988,683 B2 | 8/2011 | Adair et al. |
| 7,993,300 B2 | 8/2011 | Nyholm et al. |
| 7,993,301 B2 | 8/2011 | Boyd et al. |
| 7,998,111 B2 | 8/2011 | Moberg et al. |
| 8,021,357 B2 | 9/2011 | Tanaka et al. |
| 8,025,658 B2 | 9/2011 | Chong et al. |
| 8,029,469 B2 | 10/2011 | Ethelfeld |
| 8,034,019 B2 | 10/2011 | Nair et al. |
| 8,038,666 B2 | 10/2011 | Triplett et al. |
| 8,057,431 B2 | 11/2011 | Woehr et al. |
| 8,057,436 B2 | 11/2011 | Causey et al. |
| 8,062,253 B2 | 11/2011 | Nielsen et al. |
| 8,062,257 B2 | 11/2011 | Moberg et al. |
| 8,065,096 B2 | 11/2011 | Moberg et al. |
| 8,066,694 B2 | 11/2011 | Wagener |
| D650,079 S | 12/2011 | Presta et al. |
| D650,903 S | 12/2011 | Kosinski et al. |
| 8,086,306 B2 | 12/2011 | Katzman et al. |
| D652,503 S | 1/2012 | Cameron et al. |
| 8,105,279 B2 | 1/2012 | Mernoe et al. |
| 8,114,046 B2 | 2/2012 | Covino et al. |
| 8,114,064 B2 | 2/2012 | Alferness et al. |
| 8,114,066 B2 | 2/2012 | Naef et al. |
| D657,462 S | 4/2012 | Siroky |
| 8,147,446 B2 | 4/2012 | Yodat et al. |
| 8,152,764 B2 | 4/2012 | Istoc et al. |
| 8,152,770 B2 | 4/2012 | Reid |
| 8,152,779 B2 | 4/2012 | Cabiri |
| 8,152,793 B2 | 4/2012 | Keinaenen et al. |
| 8,157,693 B2 | 4/2012 | Waksmundzki |
| 8,157,769 B2 | 4/2012 | Cabiri |
| 8,162,674 B2 | 4/2012 | Cho et al. |
| 8,162,923 B2 | 4/2012 | Adams et al. |
| 8,167,841 B2 | 5/2012 | Teisen-Simony et al. |
| 8,172,591 B2 | 5/2012 | Wertz |
| 8,172,804 B2 | 5/2012 | Bikovsky |

(56) References Cited

U.S. PATENT DOCUMENTS

| | | |
|---|---|---|
| 8,182,447 B2 | 5/2012 | Moberg et al. |
| 8,182,462 B2 | 5/2012 | Istoc et al. |
| 8,197,444 B1 | 6/2012 | Bazargan et al. |
| 8,206,351 B2 | 6/2012 | Sugimoto et al. |
| 8,221,356 B2 | 7/2012 | Enggaard et al. |
| 8,267,893 B2 | 9/2012 | Moberg et al. |
| 8,267,921 B2 | 9/2012 | Yodat et al. |
| 8,287,520 B2 | 10/2012 | Drew et al. |
| 8,292,647 B1 | 10/2012 | Mcgrath et al. |
| 8,308,679 B2 | 11/2012 | Hanson et al. |
| 8,323,250 B2 | 12/2012 | Chong et al. |
| 8,348,898 B2 | 1/2013 | Cabiri |
| 8,372,039 B2 | 2/2013 | Mernoe et al. |
| 8,373,421 B2 | 2/2013 | Lindegger et al. |
| 8,409,142 B2 | 4/2013 | Causey et al. |
| 8,414,557 B2 | 4/2013 | Istoc et al. |
| 8,430,847 B2 | 4/2013 | Mernoe et al. |
| D685,083 S | 6/2013 | Schneider et al. |
| 8,465,455 B2 | 6/2013 | Cabiri |
| 8,469,942 B2 | 6/2013 | Kow et al. |
| D687,141 S | 7/2013 | Schneider et al. |
| 8,474,332 B2 | 7/2013 | Bente et al. |
| 8,475,408 B2 | 7/2013 | Mernoe et al. |
| 8,479,595 B2 | 7/2013 | Vazquez et al. |
| 8,483,980 B2 | 7/2013 | Moberg et al. |
| 8,495,918 B2 | 7/2013 | Bazargan et al. |
| 8,496,862 B2 | 7/2013 | Zelkovich et al. |
| D687,536 S | 8/2013 | Guarraia et al. |
| 8,512,287 B2 | 8/2013 | Cindrich et al. |
| 8,517,987 B2 | 8/2013 | Istoc et al. |
| 8,523,803 B1 | 9/2013 | Favreau |
| D692,552 S | 10/2013 | Lovell et al. |
| 8,556,856 B2 | 10/2013 | Bazargan et al. |
| 8,562,364 B2 | 10/2013 | Lin et al. |
| 8,574,216 B2 | 11/2013 | Istoc et al. |
| 8,603,026 B2 | 12/2013 | Favreau |
| 8,603,027 B2 | 12/2013 | Favreau |
| 8,617,110 B2 | 12/2013 | Moberg et al. |
| 8,628,510 B2 | 1/2014 | Bazargan et al. |
| 8,647,074 B2 | 2/2014 | Moberg et al. |
| 8,647,296 B2 | 2/2014 | Moberg et al. |
| 8,668,672 B2 | 3/2014 | Moberg et al. |
| 8,674,288 B2 | 3/2014 | Hanson et al. |
| 8,679,060 B2 | 3/2014 | Mernoe et al. |
| 8,681,010 B2 | 3/2014 | Moberg et al. |
| 8,690,855 B2 | 4/2014 | Alderete et al. |
| 8,708,961 B2 | 4/2014 | Field et al. |
| 8,751,237 B2 | 6/2014 | Kubota |
| 8,753,326 B2 | 6/2014 | Chong et al. |
| 8,753,331 B2 | 6/2014 | Murphy |
| 8,764,707 B2 | 7/2014 | Moberg et al. |
| 8,764,723 B2 | 7/2014 | Chong et al. |
| 8,771,222 B2 | 7/2014 | Kanderian et al. |
| 8,777,896 B2 | 7/2014 | Starkweather et al. |
| 8,777,924 B2 | 7/2014 | Kanderian et al. |
| 8,777,925 B2 | 7/2014 | Patton |
| 8,784,369 B2 | 7/2014 | Starkweather et al. |
| 8,784,370 B2 | 7/2014 | Lebel et al. |
| 8,790,295 B1 | 7/2014 | Sigg et al. |
| 8,795,224 B2 | 8/2014 | Starkweather et al. |
| 8,795,231 B2 | 8/2014 | Chong et al. |
| 8,795,260 B2 | 8/2014 | Drew |
| 8,801,668 B2 | 8/2014 | Ali et al. |
| 8,801,679 B2 | 8/2014 | Iio et al. |
| 8,810,394 B2 | 8/2014 | Kalpin |
| 8,814,379 B2 | 8/2014 | Griffiths et al. |
| 8,915,882 B2 | 12/2014 | Cabiri |
| 8,920,374 B2 | 12/2014 | Bokelman et al. |
| D723,157 S | 2/2015 | Clemente et al. |
| 9,061,104 B2 | 6/2015 | Daniel |
| 9,061,110 B2 | 6/2015 | Avery et al. |
| 9,072,827 B2 | 7/2015 | Cabiri |
| 9,089,475 B2 | 7/2015 | Fangrow |
| 9,089,641 B2 | 7/2015 | Kavazov |
| 9,149,575 B2 | 10/2015 | Cabiri |
| 9,393,365 B2 | 7/2016 | Cabiri |
| D768,288 S | 10/2016 | O'Connor et al. |
| 9,463,280 B2 | 10/2016 | Cabiri |
| 9,492,610 B2 | 11/2016 | Cabiri |
| D774,640 S | 12/2016 | Tyce et al. |
| 9,511,190 B2 | 12/2016 | Cabiri |
| 9,522,234 B2 | 12/2016 | Cabiri |
| D776,262 S | 1/2017 | Tyce et al. |
| D776,263 S | 1/2017 | Tyce et al. |
| D776,264 S | 1/2017 | Tyce et al. |
| D776,265 S | 1/2017 | Tyce et al. |
| 9,572,926 B2 | 2/2017 | Cabiri |
| 9,707,335 B2 | 7/2017 | Agard et al. |
| D794,776 S | 8/2017 | Tyce et al. |
| 9,737,655 B2 | 8/2017 | Clemente et al. |
| 9,782,545 B2 | 10/2017 | Gross et al. |
| 9,802,030 B2 | 10/2017 | Clemente et al. |
| D804,019 S | 11/2017 | Costello et al. |
| 9,814,832 B2 | 11/2017 | Agard et al. |
| D804,650 S | 12/2017 | Costello et al. |
| D805,186 S | 12/2017 | Costello et al. |
| D805,187 S | 12/2017 | Costello et al. |
| D805,188 S | 12/2017 | Costello et al. |
| D805,189 S | 12/2017 | Costello et al. |
| D805,190 S | 12/2017 | Costello et al. |
| 9,861,759 B2 | 1/2018 | Gross et al. |
| D810,278 S | 2/2018 | Cabiri et al. |
| D810,279 S | 2/2018 | Cabiri et al. |
| D811,583 S | 2/2018 | Cabiri et al. |
| D811,584 S | 2/2018 | Cabiri et al. |
| D817,481 S | 5/2018 | Cabiri et al. |
| D851,752 S | 6/2019 | Nazzaro et al. |
| D865,945 S | 11/2019 | Nazzaro et al. |
| 2001/0025168 A1 | 9/2001 | Gross et al. |
| 2001/0041869 A1 | 11/2001 | Causey et al. |
| 2002/0010423 A1 | 1/2002 | Gross et al. |
| 2002/0029018 A1 | 3/2002 | Jeffrey |
| 2002/0040208 A1 | 4/2002 | Flaherty et al. |
| 2002/0043951 A1 | 4/2002 | Moberg |
| 2002/0055711 A1 | 5/2002 | Lavi et al. |
| 2002/0065488 A1 | 5/2002 | Suzuki et al. |
| 2002/0100472 A1* | 8/2002 | Casper ............ A61M 15/0068 128/200.14 |
| 2002/0107487 A1 | 8/2002 | Preuthun |
| 2002/0123740 A1 | 9/2002 | Flaherty et al. |
| 2002/0161332 A1 | 10/2002 | Ramey |
| 2002/0169215 A1 | 11/2002 | Meng |
| 2003/0009133 A1 | 1/2003 | Ramey |
| 2003/0109827 A1 | 6/2003 | Lavi et al. |
| 2003/0125671 A1 | 7/2003 | Aramata et al. |
| 2003/0135159 A1 | 7/2003 | Daily et al. |
| 2003/0160683 A1 | 8/2003 | Blomquist |
| 2003/0171717 A1 | 9/2003 | Farrugia et al. |
| 2003/0181868 A1 | 9/2003 | Swenson |
| 2003/0199825 A1 | 10/2003 | Flaherty |
| 2003/0199827 A1 | 10/2003 | Thorne |
| 2003/0236498 A1 | 12/2003 | Gross et al. |
| 2004/0010207 A1 | 1/2004 | Flaherty et al. |
| 2004/0015131 A1 | 1/2004 | Flaherty et al. |
| 2004/0064088 A1 | 4/2004 | Gorman et al. |
| 2004/0085215 A1 | 5/2004 | Moberg et al. |
| 2004/0092873 A1 | 5/2004 | Moberg |
| 2004/0116866 A1 | 6/2004 | Gorman et al. |
| 2004/0127857 A1 | 7/2004 | Shemesh et al. |
| 2004/0158172 A1 | 8/2004 | Hancock |
| 2004/0186419 A1 | 9/2004 | Cho |
| 2004/0186424 A1 | 9/2004 | Hjertman |
| 2004/0260233 A1 | 12/2004 | Garibotto et al. |
| 2005/0033234 A1 | 2/2005 | Sadowski et al. |
| 2005/0049553 A1 | 3/2005 | Triplett et al. |
| 2005/0065466 A1 | 3/2005 | Vedrine |
| 2005/0065472 A1 | 3/2005 | Cindrich et al. |
| 2005/0070845 A1 | 3/2005 | Faries et al. |
| 2005/0071487 A1 | 3/2005 | Lu et al. |
| 2005/0113761 A1 | 5/2005 | Faust et al. |
| 2005/0159706 A1 | 7/2005 | Wilkinson et al. |
| 2005/0171476 A1 | 8/2005 | Judson et al. |
| 2005/0171512 A1 | 8/2005 | Flaherty |
| 2005/0177136 A1 | 8/2005 | Miller |

(56) References Cited

U.S. PATENT DOCUMENTS

| | | |
|---|---|---|
| 2005/0197650 A1 | 9/2005 | Sugimoto et al. |
| 2005/0203461 A1 | 9/2005 | Flaherty et al. |
| 2005/0238507 A1 | 10/2005 | Diianni et al. |
| 2005/0283114 A1 | 12/2005 | Bresina et al. |
| 2006/0013716 A1 | 1/2006 | Nason et al. |
| 2006/0030816 A1 | 2/2006 | Zubry |
| 2006/0095014 A1 | 5/2006 | Ethelfeld |
| 2006/0122577 A1 | 6/2006 | Poulsen et al. |
| 2006/0173406 A1 | 8/2006 | Hayes et al. |
| 2006/0173408 A1 | 8/2006 | Wyrick |
| 2006/0173410 A1 | 8/2006 | Moberg et al. |
| 2006/0173439 A1 | 8/2006 | Thorne et al. |
| 2006/0184154 A1 | 8/2006 | Moberg et al. |
| 2006/0195029 A1 | 8/2006 | Shults et al. |
| 2006/0211982 A1 | 9/2006 | Prestrelski et al. |
| 2006/0229569 A1 | 10/2006 | Lavi et al. |
| 2006/0264831 A1 | 11/2006 | Skwarek et al. |
| 2006/0264889 A1 | 11/2006 | Moberg et al. |
| 2006/0264890 A1 | 11/2006 | Moberg et al. |
| 2006/0264894 A1 | 11/2006 | Moberg et al. |
| 2006/0270987 A1 | 11/2006 | Peter |
| 2006/0283465 A1 | 12/2006 | Nickel et al. |
| 2006/0293722 A1 | 12/2006 | Slatkine et al. |
| 2007/0016381 A1 | 1/2007 | Kamath et al. |
| 2007/0021733 A1 | 1/2007 | Hansen et al. |
| 2007/0049865 A1 | 3/2007 | Radmer et al. |
| 2007/0073228 A1 | 3/2007 | Mernoe et al. |
| 2007/0106218 A1 | 5/2007 | Yodfat et al. |
| 2007/0118405 A1 | 5/2007 | Campbell et al. |
| 2007/0123819 A1 | 5/2007 | Mernoe et al. |
| 2007/0129688 A1 | 6/2007 | Scheurer et al. |
| 2007/0149926 A1 | 6/2007 | Moberg et al. |
| 2007/0167912 A1 | 7/2007 | Causey et al. |
| 2007/0185449 A1 | 8/2007 | Mernoe |
| 2007/0191770 A1 | 8/2007 | Moberg et al. |
| 2007/0197968 A1 | 8/2007 | Pongpairochana et al. |
| 2007/0203454 A1 | 8/2007 | Shermer et al. |
| 2007/0219480 A1 | 9/2007 | Kamen et al. |
| 2007/0233038 A1 | 10/2007 | Pruitt et al. |
| 2007/0282269 A1 | 12/2007 | Carter et al. |
| 2008/0021439 A1 | 1/2008 | Brittingham et al. |
| 2008/0033367 A1 | 2/2008 | Haury et al. |
| 2008/0033369 A1 | 2/2008 | Kohlbrenner et al. |
| 2008/0033393 A1 | 2/2008 | Edwards et al. |
| 2008/0051710 A1 | 2/2008 | Moberg et al. |
| 2008/0051711 A1 | 2/2008 | Mounce et al. |
| 2008/0051727 A1 | 2/2008 | Moberg et al. |
| 2008/0051730 A1 | 2/2008 | Bikovsky |
| 2008/0059133 A1 | 3/2008 | Edwards et al. |
| 2008/0097381 A1 | 4/2008 | Moberg et al. |
| 2008/0099015 A1* | 5/2008 | Pocock ............ A61M 15/0008 128/203.15 |
| 2008/0108951 A1 | 5/2008 | Jerde et al. |
| 2008/0125700 A1 | 5/2008 | Moberg et al. |
| 2008/0140006 A1 | 6/2008 | Eskuri et al. |
| 2008/0140018 A1 | 6/2008 | Enggaard et al. |
| 2008/0147004 A1 | 6/2008 | Mann et al. |
| 2008/0156476 A1 | 7/2008 | Smisson et al. |
| 2008/0167641 A1 | 7/2008 | Hansen et al. |
| 2008/0188813 A1 | 8/2008 | Miller et al. |
| 2008/0195049 A1 | 8/2008 | Thalmann et al. |
| 2008/0208138 A1 | 8/2008 | Lim et al. |
| 2008/0215006 A1 | 9/2008 | Thorkild |
| 2008/0215015 A1 | 9/2008 | Cindrich et al. |
| 2008/0221522 A1 | 9/2008 | Moberg et al. |
| 2008/0221523 A1 | 9/2008 | Moberg et al. |
| 2008/0234627 A1 | 9/2008 | Dent et al. |
| 2008/0243087 A1 | 10/2008 | Enggaard et al. |
| 2008/0249473 A1 | 10/2008 | Rutti et al. |
| 2008/0255516 A1 | 10/2008 | Yodfat et al. |
| 2008/0262436 A1 | 10/2008 | Olson |
| 2008/0269687 A1 | 10/2008 | Chong et al. |
| 2008/0269723 A1 | 10/2008 | Mastrototaro et al. |
| 2008/0274630 A1 | 11/2008 | Shelton et al. |
| 2008/0275407 A1 | 11/2008 | Scheurer |
| 2008/0281270 A1 | 11/2008 | Cross et al. |
| 2008/0294143 A1 | 11/2008 | Tanaka et al. |
| 2008/0306449 A1 | 12/2008 | Kristensen et al. |
| 2008/0312601 A1 | 12/2008 | Cane |
| 2008/0319416 A1 | 12/2008 | Yodat et al. |
| 2009/0041805 A1 | 2/2009 | Walker |
| 2009/0043253 A1 | 2/2009 | Podaima |
| 2009/0048347 A1 | 2/2009 | Cohen et al. |
| 2009/0054750 A1 | 2/2009 | Jennewine |
| 2009/0054852 A1 | 2/2009 | Takano et al. |
| 2009/0062767 A1 | 3/2009 | Van et al. |
| 2009/0069784 A1 | 3/2009 | Estes et al. |
| 2009/0076360 A1 | 3/2009 | Brister et al. |
| 2009/0076453 A1 | 3/2009 | Mejlhede et al. |
| 2009/0088694 A1 | 4/2009 | Carter et al. |
| 2009/0088731 A1 | 4/2009 | Campbell et al. |
| 2009/0093792 A1 | 4/2009 | Gross et al. |
| 2009/0093793 A1 | 4/2009 | Gross et al. |
| 2009/0105650 A1 | 4/2009 | Wiegel et al. |
| 2009/0124977 A1 | 5/2009 | Jensen |
| 2009/0131860 A1 | 5/2009 | Nielsen |
| 2009/0139724 A1 | 6/2009 | Gray et al. |
| 2009/0143730 A1 | 6/2009 | De et al. |
| 2009/0143735 A1 | 6/2009 | De Polo et al. |
| 2009/0149830 A1 | 6/2009 | Spector |
| 2009/0182277 A1 | 7/2009 | Carter |
| 2009/0204076 A1 | 8/2009 | Liversidge |
| 2009/0209896 A1 | 8/2009 | Selevan |
| 2009/0216103 A1 | 8/2009 | Brister et al. |
| 2009/0234319 A1 | 9/2009 | Marksteiner |
| 2009/0240240 A1 | 9/2009 | Hines et al. |
| 2009/0243234 A1 | 10/2009 | Sharif |
| 2009/0253973 A1 | 10/2009 | Bashan et al. |
| 2009/0259176 A1 | 10/2009 | Yairi |
| 2009/0281585 A1 | 11/2009 | Katzman et al. |
| 2009/0299290 A1 | 12/2009 | Moberg |
| 2009/0299397 A1 | 12/2009 | Ruan et al. |
| 2009/0326459 A1 | 12/2009 | Shipway et al. |
| 2009/0326509 A1 | 12/2009 | Muse et al. |
| 2010/0030156 A1 | 2/2010 | Beebe et al. |
| 2010/0030198 A1 | 2/2010 | Beebe et al. |
| 2010/0037680 A1 | 2/2010 | Moberg et al. |
| 2010/0044270 A1* | 2/2010 | Noble ............ B65D 83/04 206/538 |
| 2010/0049128 A1 | 2/2010 | Mckenzie et al. |
| 2010/0049144 A1 | 2/2010 | Mcconnell et al. |
| 2010/0057057 A1 | 3/2010 | Hayter et al. |
| 2010/0076412 A1 | 3/2010 | Rush et al. |
| 2010/0081993 A1 | 4/2010 | O'Connor |
| 2010/0094255 A1 | 4/2010 | Nycz et al. |
| 2010/0100076 A1 | 4/2010 | Rush et al. |
| 2010/0100077 A1 | 4/2010 | Rush et al. |
| 2010/0106098 A1 | 4/2010 | Atterbury et al. |
| 2010/0121314 A1 | 5/2010 | Iobbi |
| 2010/0137790 A1 | 6/2010 | Yodfat |
| 2010/0137831 A1 | 6/2010 | Tsais |
| 2010/0145303 A1 | 6/2010 | Yodfat et al. |
| 2010/0145305 A1 | 6/2010 | Alon |
| 2010/0152658 A1 | 6/2010 | Hanson et al. |
| 2010/0162548 A1 | 7/2010 | Leidig |
| 2010/0168607 A1 | 7/2010 | Miesel |
| 2010/0168683 A1 | 7/2010 | Cabiri |
| 2010/0198157 A1 | 8/2010 | Gyrn et al. |
| 2010/0204657 A1 | 8/2010 | Yodfat et al. |
| 2010/0211011 A1 | 8/2010 | Haar |
| 2010/0217192 A1 | 8/2010 | Moberg et al. |
| 2010/0217193 A1 | 8/2010 | Moberg et al. |
| 2010/0234767 A1 | 9/2010 | Sarstedt |
| 2010/0234805 A1 | 9/2010 | Kaufmann et al. |
| 2010/0234830 A1 | 9/2010 | Straessler et al. |
| 2010/0241065 A1 | 9/2010 | Moberg et al. |
| 2010/0264931 A1 | 10/2010 | Lindegger et al. |
| 2010/0274112 A1 | 10/2010 | Hoss et al. |
| 2010/0274192 A1 | 10/2010 | Mernoe |
| 2010/0274202 A1 | 10/2010 | Hyde et al. |
| 2010/0276411 A1 | 11/2010 | Hansen et al. |
| 2010/0280499 A1 | 11/2010 | Yodfat et al. |
| 2010/0331826 A1 | 12/2010 | Field et al. |
| 2011/0034900 A1 | 2/2011 | Yodfat et al. |

(56) References Cited

U.S. PATENT DOCUMENTS

| | | |
|---|---|---|
| 2011/0054399 A1 | 3/2011 | Chong et al. |
| 2011/0054400 A1 | 3/2011 | Chong et al. |
| 2011/0060284 A1 | 3/2011 | Harr |
| 2011/0066131 A1 | 3/2011 | Cabiri |
| 2011/0119033 A1 | 5/2011 | Moberg et al. |
| 2011/0125056 A1 | 5/2011 | Merchant |
| 2011/0137239 A1 | 6/2011 | DeBelser et al. |
| 2011/0144584 A1 | 6/2011 | Wozencroft |
| 2011/0160654 A1 | 6/2011 | Hanson et al. |
| 2011/0160655 A1 | 6/2011 | Hanson et al. |
| 2011/0160666 A1 | 6/2011 | Hanson et al. |
| 2011/0160669 A1 | 6/2011 | Gyrn et al. |
| 2011/0172645 A1 | 7/2011 | Moga et al. |
| 2011/0172745 A1 | 7/2011 | Na et al. |
| 2011/0178463 A1 | 7/2011 | Cabiri |
| 2011/0178472 A1 | 7/2011 | Cabiri |
| 2011/0184342 A1 | 7/2011 | Pesach et al. |
| 2011/0201998 A1 | 8/2011 | Pongpairochana et al. |
| 2011/0224614 A1 | 9/2011 | Moberg et al. |
| 2011/0238031 A1 | 9/2011 | Mair et al. |
| 2011/0245773 A1 | 10/2011 | Estes et al. |
| 2011/0264383 A1 | 10/2011 | Moberg et al. |
| 2011/0270160 A1 | 11/2011 | Mernoe |
| 2011/0282282 A1 | 11/2011 | Lorenzen et al. |
| 2011/0282296 A1 | 11/2011 | Harms et al. |
| 2011/0295205 A1 | 12/2011 | Kaufmann et al. |
| 2011/0313238 A1 | 12/2011 | Reichenbach et al. |
| 2011/0313351 A1 | 12/2011 | Kamen et al. |
| 2011/0319861 A1 | 12/2011 | Wilk |
| 2011/0319919 A1 | 12/2011 | Curry et al. |
| 2012/0004602 A1 | 1/2012 | Hanson et al. |
| 2012/0010594 A1 | 1/2012 | Holt et al. |
| 2012/0022344 A1 | 1/2012 | Kube |
| 2012/0022499 A1 | 1/2012 | Anderson et al. |
| 2012/0025995 A1 | 2/2012 | Moberg et al. |
| 2012/0029431 A1 | 2/2012 | Hwang et al. |
| 2012/0035546 A1 | 2/2012 | Cabiri |
| 2012/0041364 A1 | 2/2012 | Smith |
| 2012/0041370 A1 | 2/2012 | Moberg et al. |
| 2012/0041414 A1 | 2/2012 | Estes et al. |
| 2012/0059332 A1 | 3/2012 | Woehr et al. |
| 2012/0071819 A1 | 3/2012 | Brueggemann et al. |
| 2012/0071828 A1 | 3/2012 | Tojo et al. |
| 2012/0096953 A1 | 4/2012 | Bente et al. |
| 2012/0096954 A1 | 4/2012 | Vazquez et al. |
| 2012/0101436 A1 | 4/2012 | Bazargan et al. |
| 2012/0108933 A1 | 5/2012 | Liang et al. |
| 2012/0129362 A1 | 5/2012 | Hampo et al. |
| 2012/0132203 A1* | 5/2012 | Hodson ............. A61M 15/0065 128/203.15 |
| 2012/0160033 A1 | 6/2012 | Kow et al. |
| 2012/0165733 A1 | 6/2012 | Bazargan et al. |
| 2012/0165780 A1 | 6/2012 | Bazargan et al. |
| 2012/0215169 A1 | 8/2012 | Moberg et al. |
| 2012/0215199 A1 | 8/2012 | Moberg et al. |
| 2012/0226234 A1 | 9/2012 | Bazargan et al. |
| 2012/0259282 A1 | 10/2012 | Alderete et al. |
| 2012/0310153 A1 | 12/2012 | Moberg et al. |
| 2013/0012875 A1 | 1/2013 | Gross et al. |
| 2013/0060233 A1 | 3/2013 | O'Connor et al. |
| 2013/0068319 A1 | 3/2013 | Plumptre et al. |
| 2013/0085457 A1 | 4/2013 | Schiff et al. |
| 2013/0089992 A1 | 4/2013 | Yang |
| 2013/0096509 A1 | 4/2013 | Avery et al. |
| 2013/0110049 A1 | 5/2013 | Cronenberg et al. |
| 2013/0133438 A1 | 5/2013 | Kow et al. |
| 2013/0175192 A1 | 7/2013 | Iio et al. |
| 2013/0218089 A1 | 8/2013 | Davies et al. |
| 2013/0218092 A1 | 8/2013 | Davies et al. |
| 2013/0237953 A1 | 9/2013 | Kow et al. |
| 2013/0245595 A1 | 9/2013 | Kow et al. |
| 2013/0245596 A1 | 9/2013 | Cabiri et al. |
| 2013/0253419 A1 | 9/2013 | Favreau |
| 2013/0253420 A1 | 9/2013 | Favreau |
| 2013/0253421 A1 | 9/2013 | Favreau |
| 2013/0253472 A1 | 9/2013 | Cabiri |
| 2013/0296792 A1 | 11/2013 | Cabiri |
| 2013/0296799 A1 | 11/2013 | Degtiar et al. |
| 2013/0304021 A1 | 11/2013 | Cabiri et al. |
| 2013/0310753 A1 | 11/2013 | Cabiri |
| 2013/0323699 A1 | 12/2013 | Edwards et al. |
| 2013/0331791 A1 | 12/2013 | Gross et al. |
| 2014/0012229 A1* | 1/2014 | Bokelman ............ A61M 5/2033 604/154 |
| 2014/0055073 A1 | 2/2014 | Favreau |
| 2014/0055076 A1 | 2/2014 | Favreau |
| 2014/0058349 A1 | 2/2014 | Bazargan et al. |
| 2014/0083517 A1 | 3/2014 | Moia et al. |
| 2014/0094755 A1 | 4/2014 | Bazargan et al. |
| 2014/0128807 A1 | 5/2014 | Moberg et al. |
| 2014/0128815 A1 | 5/2014 | Cabiri et al. |
| 2014/0128835 A1 | 5/2014 | Moberg et al. |
| 2014/0135692 A1 | 5/2014 | Alderete et al. |
| 2014/0135694 A1 | 5/2014 | Moberg et al. |
| 2014/0142499 A1 | 5/2014 | Moberg et al. |
| 2014/0148784 A1 | 5/2014 | Anderson et al. |
| 2014/0148785 A1 | 5/2014 | Moberg et al. |
| 2014/0163522 A1 | 6/2014 | Alderete et al. |
| 2014/0171881 A1 | 6/2014 | Cabiri |
| 2014/0188073 A1 | 7/2014 | Cabiri et al. |
| 2014/0194819 A1 | 7/2014 | Maule et al. |
| 2014/0194854 A1 | 7/2014 | Tsais |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0210631 A1 | 7/2014 | Zavis |
| 2014/0213975 A1 | 7/2014 | Clemente et al. |
| 2014/0236087 A1 | 8/2014 | Alderete et al. |
| 2014/0261758 A1 | 9/2014 | Wlodarczyk et al. |
| 2014/0288511 A1 | 9/2014 | Tan-Malecki et al. |
| 2014/0330240 A1 | 11/2014 | Cabiri et al. |
| 2015/0011965 A1 | 1/2015 | Cabiri |
| 2015/0011976 A1 | 1/2015 | Vouillamoz et al. |
| 2015/0032084 A1 | 1/2015 | Cabiri |
| 2015/0057613 A1 | 2/2015 | Clemente et al. |
| 2015/0119797 A1 | 4/2015 | Cabiri |
| 2015/0174346 A1* | 6/2015 | Dhuppad ............ A61M 15/0073 128/202.13 |
| 2015/0224253 A1 | 8/2015 | Cabiri |
| 2015/0297833 A1* | 10/2015 | Henderson .......... A61M 5/2033 604/135 |
| 2015/0367074 A1* | 12/2015 | Draper .................... A61M 5/20 604/198 |
| 2016/0015910 A1 | 1/2016 | Mukai et al. |
| 2016/0058941 A1 | 3/2016 | Wu et al. |
| 2016/0199592 A1 | 7/2016 | Eggert et al. |
| 2016/0228644 A1 | 8/2016 | Cabiri |
| 2016/0256352 A1 | 9/2016 | Bar-El et al. |
| 2017/0028132 A1 | 2/2017 | Cronenberg et al. |
| 2017/0106138 A1 | 4/2017 | Cabiri |
| 2017/0224915 A1 | 8/2017 | Destefano et al. |
| 2017/0281859 A1 | 10/2017 | Agard et al. |
| 2017/0312450 A1 | 11/2017 | Gross et al. |
| 2017/0354781 A1 | 12/2017 | Cronenberg et al. |
| 2017/0354782 A1 | 12/2017 | Quinn et al. |
| 2017/0354783 A1 | 12/2017 | Gazeley et al. |
| 2017/0354785 A1 | 12/2017 | Gazeley et al. |
| 2017/0354788 A1 | 12/2017 | Quinn et al. |
| 2018/0001073 A1 | 1/2018 | Clemente et al. |
| 2018/0008769 A1 | 1/2018 | O'Connor et al. |
| 2018/0021508 A1 | 1/2018 | Destefano et al. |
| 2018/0028747 A1 | 2/2018 | Hanson et al. |
| 2018/0043091 A1 | 2/2018 | Agard et al. |
| 2018/0055995 A1 | 3/2018 | Hanson et al. |
| 2018/0221584 A1* | 8/2018 | Grimoldby ........ A61M 5/31505 |
| 2018/0236173 A1 | 8/2018 | Mccaffrey et al. |
| 2019/0091404 A1 | 3/2019 | Nazzaro et al. |
| 2019/0117880 A1 | 4/2019 | Hirschel et al. |

(56) References Cited

U.S. PATENT DOCUMENTS

| | | | |
|---|---|---|---|
| 2019/0366012 | A1 | 12/2019 | Gross et al. |
| 2020/0282144 | A1* | 9/2020 | Pearson ............ A61M 5/31576 |

FOREIGN PATENT DOCUMENTS

| | | | |
|---|---|---|---|
| CN | 1636605 | A | 7/2005 |
| CN | 1747683 | A | 3/2006 |
| CN | 1863566 | A | 11/2006 |
| CN | 1929884 | A | 3/2007 |
| CN | 101001661 | A | 7/2007 |
| CN | 101090749 | A | 12/2007 |
| CN | 101239205 | A | 8/2008 |
| CN | 101460207 | A | 6/2009 |
| CN | 101687083 | A | 3/2010 |
| CN | 101868273 | A | 10/2010 |
| CN | 101970033 | A | 2/2011 |
| CN | 201941304 | U | 8/2011 |
| CN | 102186733 | A | 9/2011 |
| CN | 102256657 | A | 11/2011 |
| CN | 102639169 | A | 8/2012 |
| CN | 104703641 | A | 6/2015 |
| CN | 104955504 | A | 9/2015 |
| DE | 1064693 | B | 9/1959 |
| EP | 0017412 | A1 | 10/1980 |
| EP | 0222656 | A1 | 5/1987 |
| EP | 0401179 | A1 | 12/1990 |
| EP | 0744975 | A1 | 12/1996 |
| EP | 1530979 | A1 | 5/2005 |
| EP | 1666080 | A1 | 6/2006 |
| EP | 2060606 | A1 | 5/2009 |
| EP | 2345441 | A1 | 7/2011 |
| EP | 2498589 | A1 | 9/2012 |
| EP | 2698180 | A1 | 2/2014 |
| EP | 2727617 | A1 | 5/2014 |
| EP | 2454483 | B1 | 8/2015 |
| JP | 07-194701 | A | 8/1995 |
| JP | 09-505758 | A | 6/1997 |
| JP | 1224341 | A | 7/1999 |
| JP | 2001-512992 | A | 8/2001 |
| JP | 2002-505601 | A | 2/2002 |
| JP | 2002-507459 | A | 3/2002 |
| JP | 2002-528676 | A | 9/2002 |
| JP | 2003-501157 | A | 1/2003 |
| JP | 2003-534061 | A | 11/2003 |
| JP | 2004-501721 | A | 1/2004 |
| JP | 2004-512100 | A | 4/2004 |
| JP | 2003-527138 | A | 8/2005 |
| JP | 2005-523127 | A | 8/2005 |
| JP | 2005-270629 | A | 10/2005 |
| JP | 2007-509661 | A | 4/2007 |
| JP | 2008100762 | A | 5/2008 |
| JP | 2008-534131 | A | 8/2008 |
| JP | 2008-220961 | A | 9/2008 |
| JP | 2009-502273 | A | 1/2009 |
| JP | 2015524722 | A | 8/2015 |
| JP | 2015536715 | A | 12/2015 |
| WO | 89/11302 | A1 | 11/1989 |
| WO | 90/09202 | A1 | 8/1990 |
| WO | 93/07922 | A1 | 4/1993 |
| WO | 94/07553 | A1 | 4/1994 |
| WO | 95/13838 | A1 | 5/1995 |
| WO | 95/21645 | A1 | 8/1995 |
| WO | 96/09083 | A1 | 3/1996 |
| WO | 96/32975 | A1 | 10/1996 |
| WO | 97/00091 | A1 | 1/1997 |
| WO | 97/10012 | A1 | 3/1997 |
| WO | 97/21457 | A1 | 6/1997 |
| WO | 97/33638 | A1 | 9/1997 |
| WO | 98/57683 | A1 | 12/1998 |
| WO | 99/29151 | A1 | 6/1999 |
| WO | 99/59665 | A1 | 11/1999 |
| WO | 00/25844 | A1 | 5/2000 |
| WO | 01/87384 | A1 | 11/2001 |
| WO | 01/89607 | A2 | 11/2001 |
| WO | 01/89613 | A1 | 11/2001 |
| WO | 02/02165 | A2 | 1/2002 |
| WO | 02/34315 | A1 | 5/2002 |
| WO | 02/72182 | A1 | 9/2002 |
| WO | 03/90833 | A1 | 11/2003 |
| WO | 2004/032990 | A2 | 4/2004 |
| WO | 2004/105841 | A1 | 12/2004 |
| WO | 2005/018703 | A2 | 3/2005 |
| WO | 2005/037350 | A2 | 4/2005 |
| WO | 2006/037434 | A1 | 4/2006 |
| WO | 2006/069380 | A1 | 6/2006 |
| WO | 2006/102676 | A1 | 9/2006 |
| WO | 2006/104806 | A2 | 10/2006 |
| WO | 2007/051563 | A1 | 5/2007 |
| WO | 2007/056504 | A1 | 5/2007 |
| WO | 2007/092618 | A2 | 8/2007 |
| WO | 2007/130868 | A1 | 11/2007 |
| WO | 2008/001377 | A2 | 1/2008 |
| WO | 2008/014908 | A1 | 2/2008 |
| WO | 2008/024810 | A2 | 2/2008 |
| WO | 2008/024814 | A2 | 2/2008 |
| WO | 2008/057976 | A2 | 5/2008 |
| WO | 2008/072229 | A2 | 6/2008 |
| WO | 2008/076459 | A1 | 6/2008 |
| WO | 2008/078318 | A2 | 7/2008 |
| WO | 2008/129549 | A1 | 10/2008 |
| WO | 2009/046989 | A2 | 4/2009 |
| WO | 2009044401 | A2 | 4/2009 |
| WO | 2009/081262 | A1 | 7/2009 |
| WO | 2009/125398 | A2 | 10/2009 |
| WO | 2009/144085 | A2 | 12/2009 |
| WO | 2010/078227 | A1 | 7/2010 |
| WO | 2010/078242 | A1 | 7/2010 |
| WO | 2011/034799 | A1 | 3/2011 |
| WO | 2011/075105 | A1 | 6/2011 |
| WO | 2011/090955 | A1 | 7/2011 |
| WO | 2011/090956 | A2 | 7/2011 |
| WO | 2011/113806 | A1 | 9/2011 |
| WO | 2011/156373 | A1 | 12/2011 |
| WO | 2012/040528 | A1 | 3/2012 |
| WO | 2012032411 | A2 | 3/2012 |
| WO | 2012160157 | A1 | 11/2012 |
| WO | 2012160160 | A1 | 11/2012 |
| WO | 2013/115843 | A1 | 8/2013 |
| WO | 2013/148270 | A2 | 10/2013 |
| WO | 2013/148435 | A1 | 10/2013 |
| WO | 2013/173092 | A1 | 11/2013 |
| WO | 2014/070453 | A1 | 5/2014 |
| WO | 2014/107408 | A1 | 7/2014 |
| WO | 2014/179210 | A1 | 11/2014 |
| WO | 2014/179774 | A1 | 11/2014 |

OTHER PUBLICATIONS

Office Action dated Oct. 28, 2011 in U.S. Appl. No. 12/615,828.
Office Action dated Oct. 28, 2015 in U.S. Appl. No. 13/429,942 by Cabiri.
Office Action dated Oct. 5, 2017 in U.S. Appl. No. 29/605,068, by Cabiri.
Office Action dated Oct. 6, 2017 in U.S. Appl. No. 29/604,616, by Cabiri.
Office Action dated Oct. 6, 2017 in U.S. Appl. No. 29/605,051, by Cabiri.
Office Action dated Oct. 9, 2014 in U.S. Appl. No. 13/873,335.
Office Action dated Sep. 13, 2017 in EP Application No. 13783458.6.
Office Action dated Sep. 18, 2015 in U.S. Appl. No. 13/874,085 by Cabiri.
Office Action dated Sep. 2, 2010 in U.S. Appl. No. 12/244,688 by Gross.
Office Action dated Sep. 2, 2014 in JP Application No. 2012-550068.
Office Action dated Sep. 2, 2014 in JP Application No. 2012-550069.
Office Action dated Sep. 29, 2013 in CN Application No. 201080040968.7.
Office Action dated Sep. 30, 2010 in U.S. Appl. No. 12/689,250, by Cabiri.

(56) References Cited

OTHER PUBLICATIONS

Office Action dated Sep. 30, 2015 in U.S. Appl. No. 13/667,739 by Cabiri.
Office Action dated Sep. 6, 2011 in U.S. Appl. No. 12/345,818.
Office Action dated Sep. 9, 2015 in U.S. Appl. No. 13/643,470 by Alon.
Office Action dated Feb. 19, 2016 in U.S. Appl. No. 14/553,399 by Cabiri.
Office Action dated Feb. 3, 2016 in U.S. Appl. No. 14/931,439 by Cabiri.
Office Action dated Jul. 1, 2016 in U.S. Appl. No. 15/132,740 by Cabiri.
Office Action dated Jul. 8, 2016 in CN Application No. 201510695320.8.
Office Action dated May 4, 2016 in U.S. Appl. No. 15/069,080 by Cabiri.
Office Action dated Nov. 6, 2015 in U.S. Appl. No. 14/715,791 by Cabiri.
U.S. Appl. No. 12/559,563, filed Sep. 15, 2009.
U.S. Appl. No. 12/689,249, filed Jan. 19, 2010.
U.S. Appl. No. 12/689,250, filed Jan. 19, 2010.
U.S. Appl. No. 13/429,840 by Cabiri, filed Mar. 26, 2012.
U.S. Appl. No. 13/429,942 by Cabiri, filed Mar. 26, 2012.
U.S. Appl. No. 13/472,112 by Cabiri, filed May 15, 2012.
U.S. Appl. No. 13/521,167 by Cabiri, filed Jul. 9, 2012.
U.S. Appl. No. 13/521,181 by Cabiri, filed Jul. 9, 2012.
U.S. Appl. No. 13/643,470 by Alon, filed Oct. 25, 2012.
U.S. Appl. No. 13/733,516 by Cabiri, filed Jan. 3, 2013.
U.S. Appl. No. 13/873,335 by Filman, filed Apr. 30, 2013.
U.S. Appl. No. 13/874,017 by Cabiri, filed Apr. 30, 2013.
U.S. Appl. No. 13/874,085 by Cabiri, filed Apr. 30, 2013.
U.S. Appl. No. 13/874,121 by Degtiar, filed Apr. 30, 2013.
U.S. Appl. No. 13/886,867 by Cabiri, filed May 3, 2013.
U.S. Appl. No. 13/892,905 by Cabiri, filed May 13, 2013.
U.S. Appl. No. 13/964,651 by Gross, filed Aug. 12, 2013.
U.S. Appl. No. 14/193,692 by Gross, filed Feb. 28, 2014.
U.S. Appl. No. 14/258,661 by Cabiri, filed Apr. 22, 2014.
U.S. Appl. No. 14/372,384 by Cabiri, filed Jul. 15, 2014.
U.S. Appl. No. 14/553,399 by Cabiri, filed Nov. 25, 2014.
U.S. Appl. No. 14/593,041 by Cabiri, filed Jan. 9, 2015.
U.S. Appl. No. 14/593,051 by Gross, filed Jan. 9, 2015.
U.S. Appl. No. 14/638,525 by Filman, filed Mar. 4, 2015.
U.S. Appl. No. 14/683,193 by Cabiri, filed Apr. 10, 2015.
U.S. Appl. No. 14/715,791 by Cabiri, filed May 19, 2015.
U.S. Appl. No. 14/725,009 by Bar-El, filed May 29, 2015.
Office Action dated Jul. 9, 2020 in European Application No. 16828833.0.
Office Action dated Sep. 29, 2019 in JP Application No. 2019-505206.
Office Action dated Sep. 27, 2020 in Chinese Application No. 201680088261.0.
Copaxone(Registered), Innovative Drugs, Teva Pharmaceuticals, downloaded from webpage http://levapharm.com/copaxone/, Download date: Jan. 2009, original posting date: unknown, 3 pages.
Daikyo Crystal Zenith(Registered) polymer, Manufactured by Daikyo Seiko, Lid. (Jun. 25, 2008).
English translation of an Office Action dated Jan. 30, 2013 in CN Application No. 200880117084.X.
English translation of an Office Action dated Mar. 5, 2014 in CN Application No. 200880117084.X.
Extended European Search Report dated Aug. 7, 2014 in EP Application No. 1417477.4.
Extended European Search Report dated Feb. 23, 2015 in EP Application No. 14166591.9.
Extended European Search Report dated Feb. 23, 2015 in EP Application No. 14166596.8.
Extended European Search Report dated Mar. 27, 2014 in EP Application No. 14154717.4.
Int'l Preliminary Report on Patentability dated Oct. 9, 2014 in Int'l Application No. PCT/US 13/31598.
Int'l Preliminary Report on Patentability dated Nov. 12, 2015 in Int'l Application No. PCT/US14/35662.
Int'l Search Report and Written Opinion dated Jan. 12, 2011 in Int'l Application No. PCT/US2010/048556; Written Opinion.
Int'l Preliminary Report on Patentability dated Apr. 7, 2010 in Int'l Application No. PCT/IL2008/001312.
Int'l Preliminary Report on Patentability dated Aug. 14, 2014 in Int'l Application No. PCT/US2012/050696.
Int'l Preliminary Report on Patentability dated Aug. 2, 2012 in Int'l Application No. PCT/US2011/021604.
Int'l Preliminary Report on Patentability dated Feb. 7, 2013 in Int'l Application No. PCT/US11/21605.
Int'l Preliminary Report on Patentability dated Jul. 16, 2015 in Int'l Application No. PCT/US2013/078040.
Int'l Preliminary Report on Patentability dated May 14, 2015 in Int'l Application No. PCT/US2013/065211.
Int'l Preliminary Report on Patentability dated Nov. 27, 2014 in Int'l Application No. PCT/US2013/039465.
Int'l Preliminary Report on Patentability dated Oct. 9, 2014 in Int'l Application No. PCT/US2013/033118.
Int'l Preliminary Report on Patentability dated Sep. 1, 2011 in Int'l Application No. PCT/US2010/048556.
Int'l Search Report and Written Opinion dated Apr. 3, 2014 in Int'l Application No. PCT/US2013/078040.
Int'l Search Report and Written Opinion dated Apr. 5, 2013 in Int'l Application No. PCT/US2012/050696.
Int'l Search Report and Written Opinion dated Aug. 28, 2014 in Int'l Application No. PCT/US2014/035662.
Int'l Search Report and Written Opinion dated Aug. 5, 2013 in Int'l Application No. PCT/US2013/033118.
Int'l Search Report and Written Opinion dated Jan. 7, 2014 in Int'l Application No. PCT/US2013/065211.
Int'l Search Report and Written Opinion dated Jul. 26, 2013 in Int'l Application No. PCT/US2012/039465.
Int'l Search Report and Written Opinion dated Jul. 31, 2014 in Int'l Application No. PCT/US2014/033598.
Int'l Search Report and Written Opinion dated Jun. 30, 2014 in Int'l Application No. PCT/US2013/031598.
Int'l Search Report and Written Opinion dated May 13, 2009 in Int'l Application No. PCT/IL2008/001312.
Int'l Search Report dated Apr. 26, 2010 in Int'l Application No. PCT/US2009/069552.
Int'l Search Report dated Jun. 17, 2011 in Int'l Application No. PCT/US2011/021604.
Int'l Search Report dated Oct. 12, 2011 in Int'l Application No. PCT/US11/21605.
Int'l Search Report dated Sep. 22, 2011 in Int'l Application No. PCT/IL11/00368; Written Opinion.
International Preliminary Report on Patentability and Written Opinion dated Jul. 5, 2011 in International Application No. PCT/US2009/069552.
Notice of Allowance dated Aug. 24, 2015 in U.S. Appl. No. 29/479,307 by Norton.
Notice of Allowance dated Apr. 25, 2016 in U.S. Appl. No. 14/553,399 by Cabiri.
Notice of Allowance dated May 11, 2016 in U.S. Appl. No. 14/931,439 by Cabiri.
Offce Action dated Sep. 21, 2010 in U.S. Appl. No. 12/244,666 by Gross.
Office Action dated Apr. 19, 2016 in U.S. Appl. No. 14/372,384 by Cabiri.
Office Action dated Apr. 24, 2013 in CN Application No. 201080040968.7.
Office Action dated Apr. 5, 2010 in U.S. Appl. No. 12/244,666 by Gross.
Office Action dated Apr. 5, 2010 in U.S. Appl. No. 12/244,688 by Gross.
Office Action dated Aug. 13, 2015 in U.S. Appl. No. 14/553,399 by Cabiri.
Office Action dated Aug. 13, 2018 in IN Application No. 857/KOLNP/2012.
Office Action dated Aug. 15, 2013 in CN Application No. 200880117084.X.

(56) References Cited

OTHER PUBLICATIONS

Office Action dated Aug. 15, 2013 in U.S. Appl. No. 13/429,942 by Cabiri.
Office Action dated Aug. 26, 2014 in CN Application No. 201180006567.4.
Office Action dated Aug. 6, 2014 in EP Appl. No. 11 707 942.6.
Office Action dated Dec. 10, 2013 in CN Application No. 201180006567.4.
Office Action dated Dec. 17, 2013 in JP Application No. 2012-529808.
Int'l Search Report and Written Opinion dated Apr. 26, 2017 in Int'l Application No. PCT/US2016/068049.
Office Action dated Dec. 29, 2016 in CN Application No. 2015106953208.
Office Action dated Dec. 3, 2015 in CN Application No. 201280068544.0.
Office Action dated Feb. 20, 2015 in U.S. Appl. No. 13/521,181 by Cabiri.
Office Action dated Feb. 21, 2012 in U.S. Appl. No. 12/689,249.
Office Action dated Feb. 24, 2015 in U.S. Appl. No. 14/258,661 by Cabiri.
Office Action dated Feb. 24, 2016 in U.S. Appl. No. 13/429,942 by Cabiri.
Office Action dated Feb. 28, 2014 in CN Application No. 201180006571.0.
Office Action dated Feb. 4, 2014 in EP Application No. 11 707 942.6.
Office Action dated Jan. 15, 2016 in U.S. Appl. No. 13/472,112 by Cabiri.
Office Action dated Jan. 16, 2014 in U.S. Appl. No. 13/429,942 by Cabiri.
Office Action dated Jan. 28, 2015 in U.S. Appl. No. 13/429,942 by Cabiri.
Office Action dated Jan. 4, 2016 in U.S. Appl. No. 13/892,905 by Cabiri.
Office Action dated Jan. 5, 2016 in U.S. Appl. No. 14/696,644 by Cabiri.
Office Action dated Jan. 8, 2013 in JP Application No. 2010-527595.
Office Action dated Jan. 8, 2014 in U.S. Appl. No. 13/521,167 by Cabiri.
Office Action dated Jul. 13, 2011 in U.S. Appl. No. 12/559,563 by Cabiri.
Office Action dated Jul. 2, 2012 in U.S. Appl. No. 13/272,555 by Cabiri.
Office Action dated Jul. 29, 2013 in JP Application No. 2012-529808.
Office Action dated Jul. 29, 2016 in U.S. Appl. No. 14/696,644, by Cabiri.
Office Action dated Jul. 31, 2015 in U.S. Appl. No. 13/521,181 by Cabiri.
Office Action dated Jul. 7, 2014 in U.S. Appl. No. 12/244,666 by Gross.
Office Action dated Jul. 7, 2016 in U.S. Appl. No. 13/892,905 by Cabiri.
Office Action dated Jun. 1, 2016 in CN Application No. 2013800274556.
Office Action dated Jun. 17, 2016 in CN Application No. 201280068544.0.
Office Action dated Jun. 3, 2014 in JP Application No. 2010-527595.
Office Action dated Jun. 4, 2015 in U.S. Appl. No. 13/667,739 by Cabiri.
Office Action dated Mar. 10, 2015 in CN Application No. 201180006567.4.
Office Action dated Mar. 10, 2015 in U.S. Appl. No. 12/244,666 by Gross.
Office Action dated Mar. 10, 2015 in U.S. Appl. No. 13/643,470 by Alon.
Office Action dated Mar. 15, 2018 in U.S. Appl. No. 29/628,592 by Cabiri.
Office Action dated Mar. 31, 2015 in JP Application No. 2012-550068.
Office Action dated May 1, 2015 in U.S. Appl. No. 14/638,525 by Filman.
Office Action dated May 13, 2015 in CN Application No. 201380025566.3.
Office Action dated May 16, 2012 in U.S. Appl. No. 12/615,828.
Office Action dated May 17, 2016 in U.S. Appl. No. 13/886,867 by Cabiri.
Office Action dated May 18, 2015 in U.S. Appl. No. 13/429,942 by Cabiri.
Office Action dated May 18, 2016 in U.S. Appl. No. 13/667,739 by Cabiri.
Office Action dated May 23, 2014 in U.S. Appl. No. 13/472,112 by Cabiri.
Office Action dated May 24, 2017 in CN Application No. 2013800571961.
Office Action dated May 3, 2012 in CN Application No. 200880117084.X.
Office Action dated May 7, 2015 in JP Application No. 2012-550069.
Office Action dated Nov. 16, 2015 in U.S. Appl. No. 13/733,516 by Cabiri.
Office Action dated Nov. 2, 2014 in CN Application No. 201180006571.0.
Office Action dated Nov. 2, 2016 in CN Application No. 2013800571961.
Office Action dated Nov. 21, 2014 in U.S. Appl. No. 13/429,840 by Cabiri.
Office Action dated Nov. 21, 2014 in U.S. Appl. No. 13/472,112 by Cabiri.
Office Action dated Nov. 25, 2015 in U.S. Appl. No. 14/372,384 by Cabiri.
Office Action dated Nov. 4, 2013 in EP Application No. 11 709 234.6.
Office Action dated Nov. 5, 2013 in JP Application No. 2010-527595.
Office Action dated Nov. 5, 2014 in U.S. Appl. No. 13/643,470 by Alon.
U.S. Appl. No. 14/850,450 by Gross, filed Sep. 10, 2015.
U.S. Appl. No. 14/861,478 by Cabiri, filed Sep. 22, 2015.
U.S. Appl. No. 14/880,673 by Cabiri, filed Oct. 12, 2015.
U.S. Appl. No. 14/931,439 by Cabiri, filed Nov. 3, 2015.
U.S. Appl. No. 15/196,775 by Cabiri, filed Jun. 29, 2016.
U.S. Appl. No. 29/479,307 by Norton, filed Jan. 14, 2014.
U.S. Appl. No. 60/997,459, filed Oct. 2, 2007.

* cited by examiner

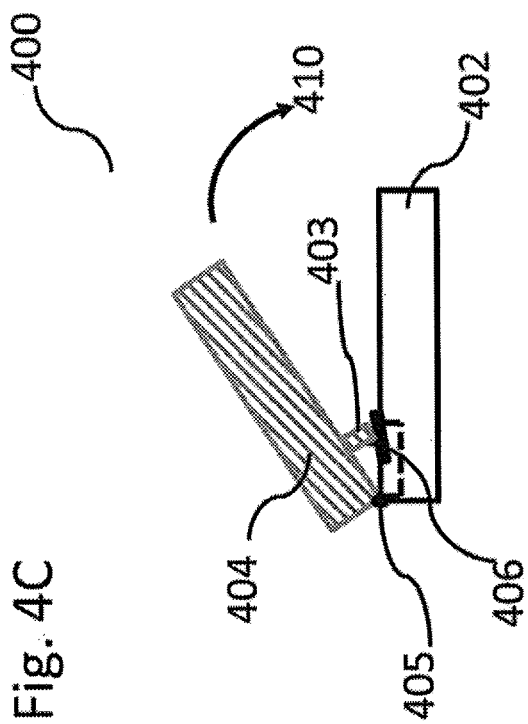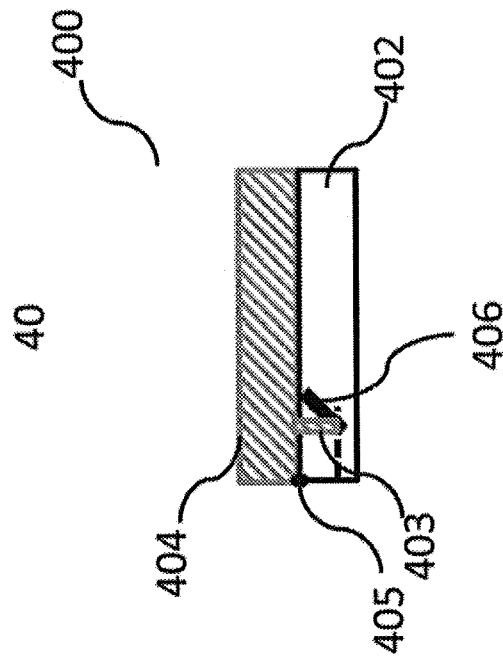
Fig. 4A  Fig. 4C
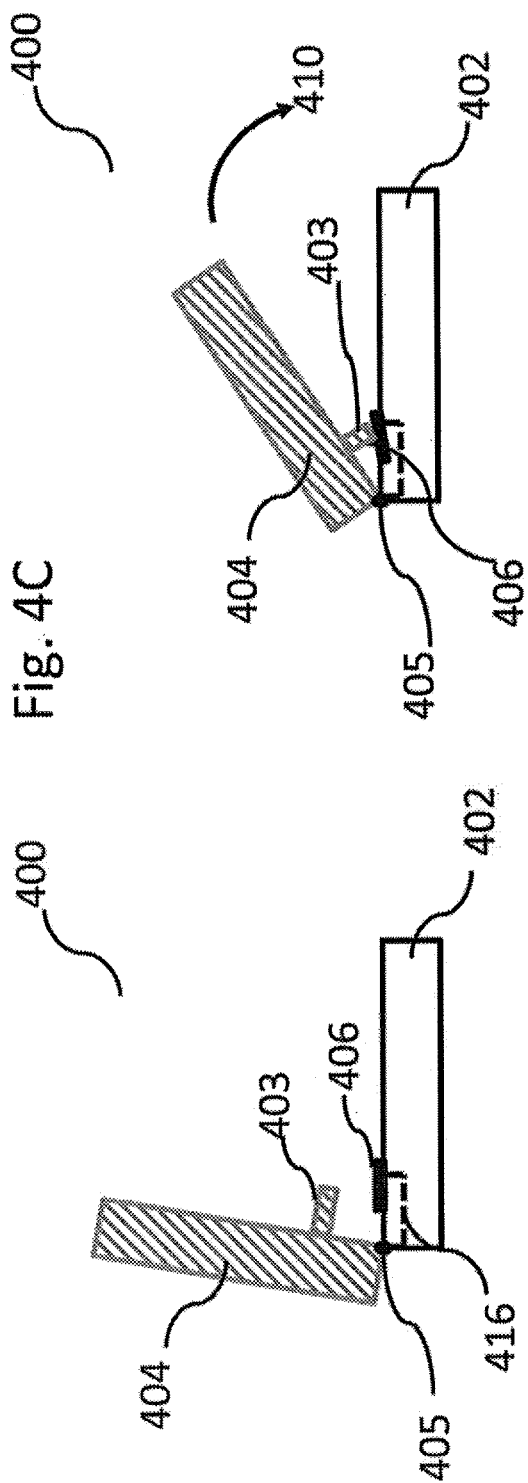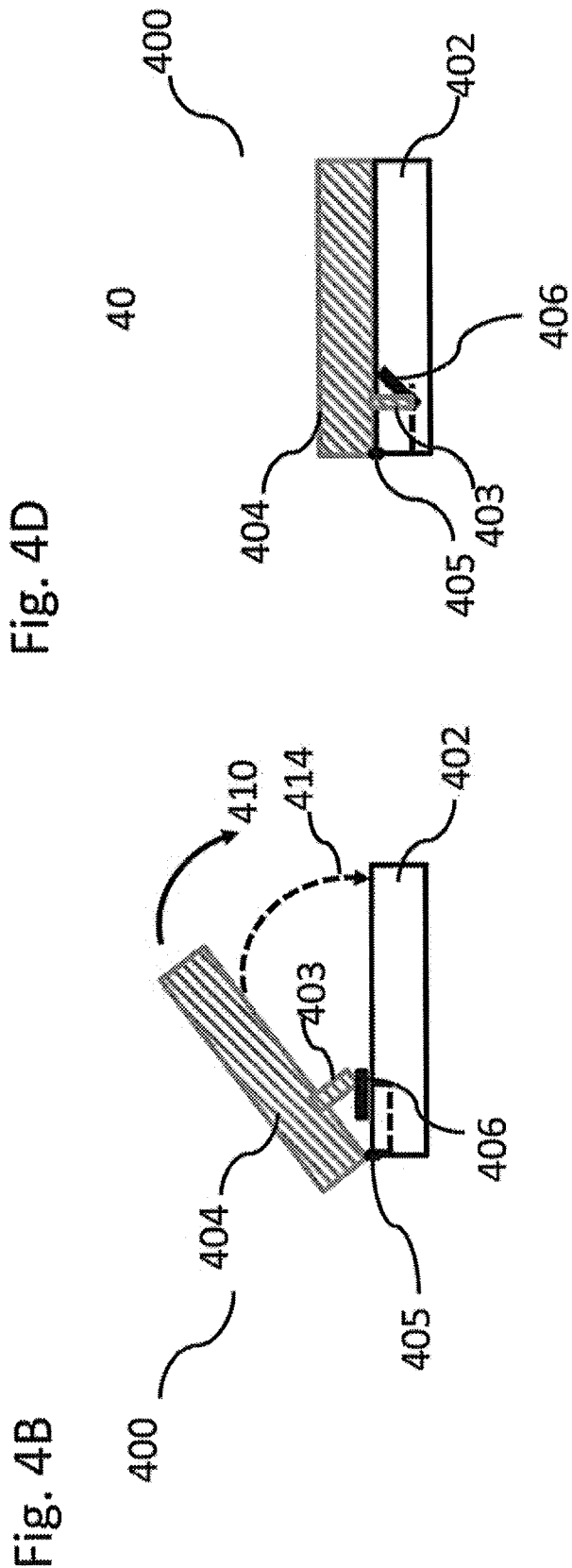
Fig. 4B  Fig. 4D

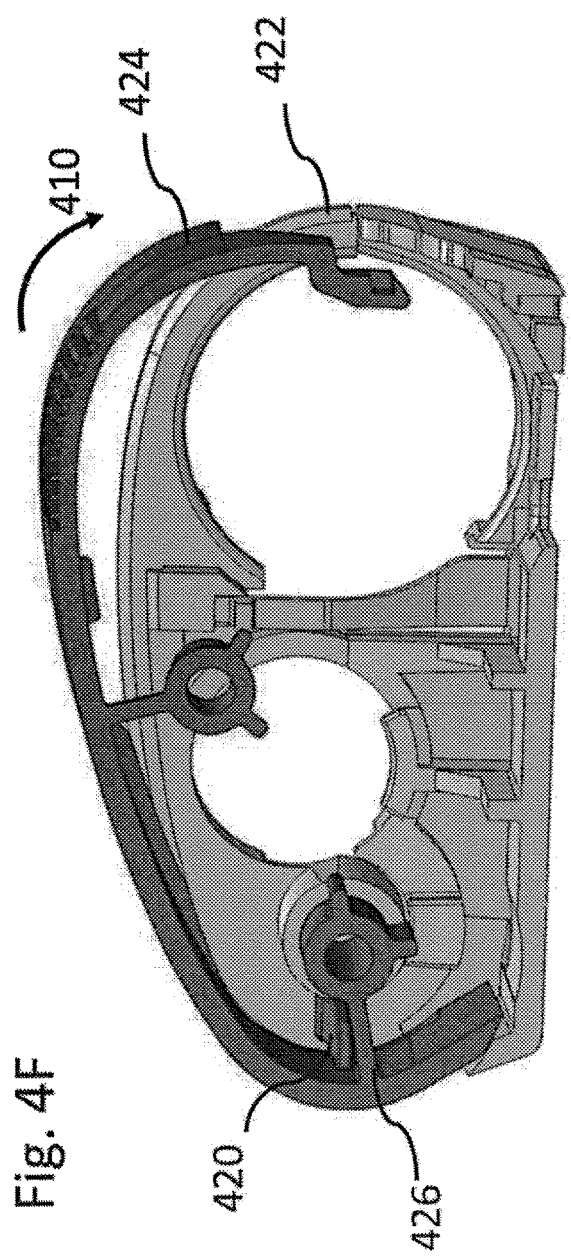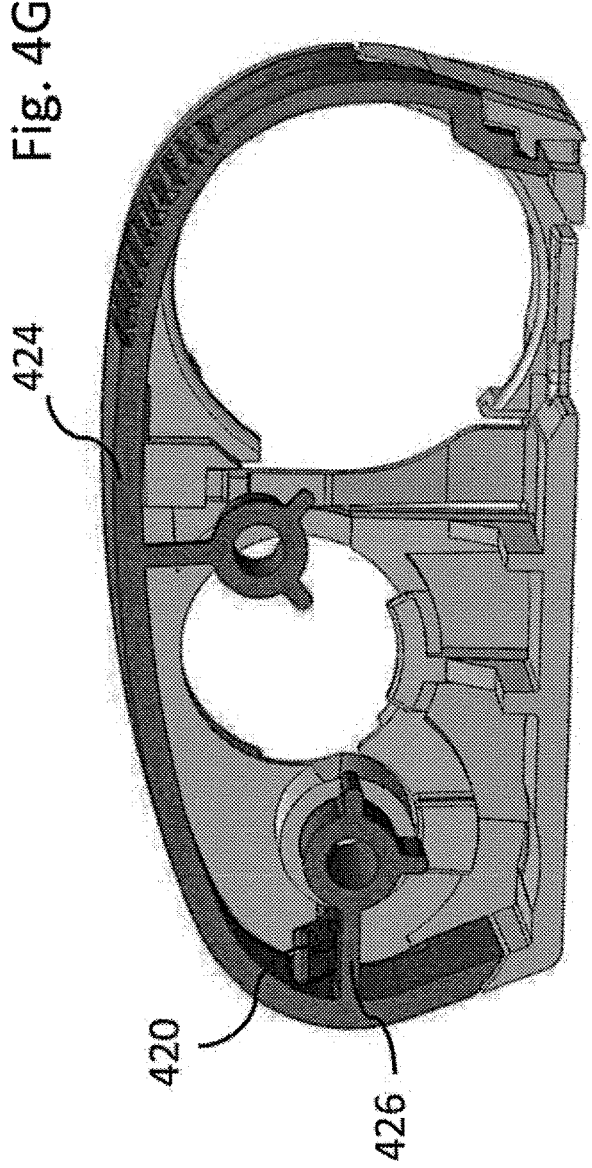

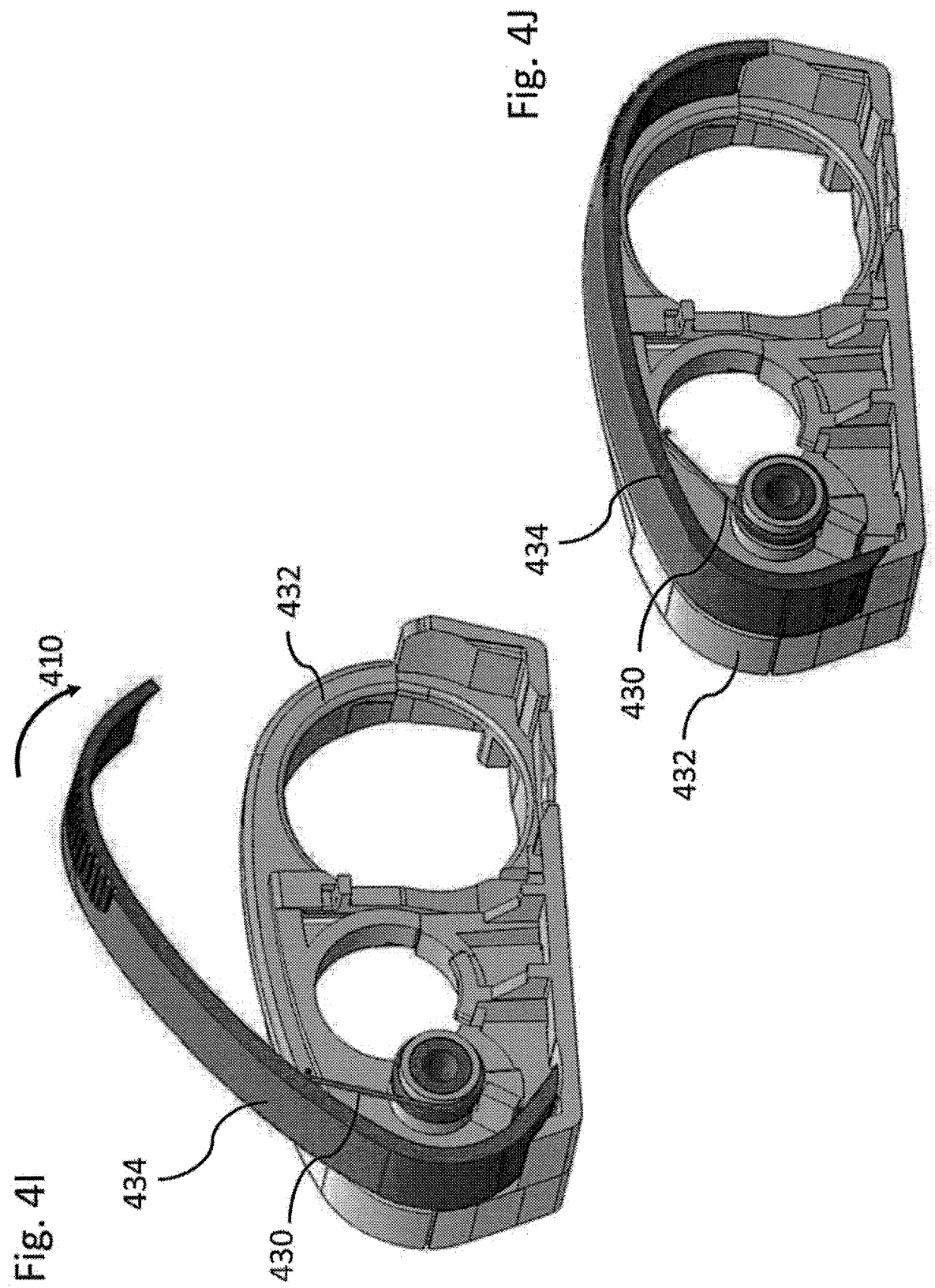

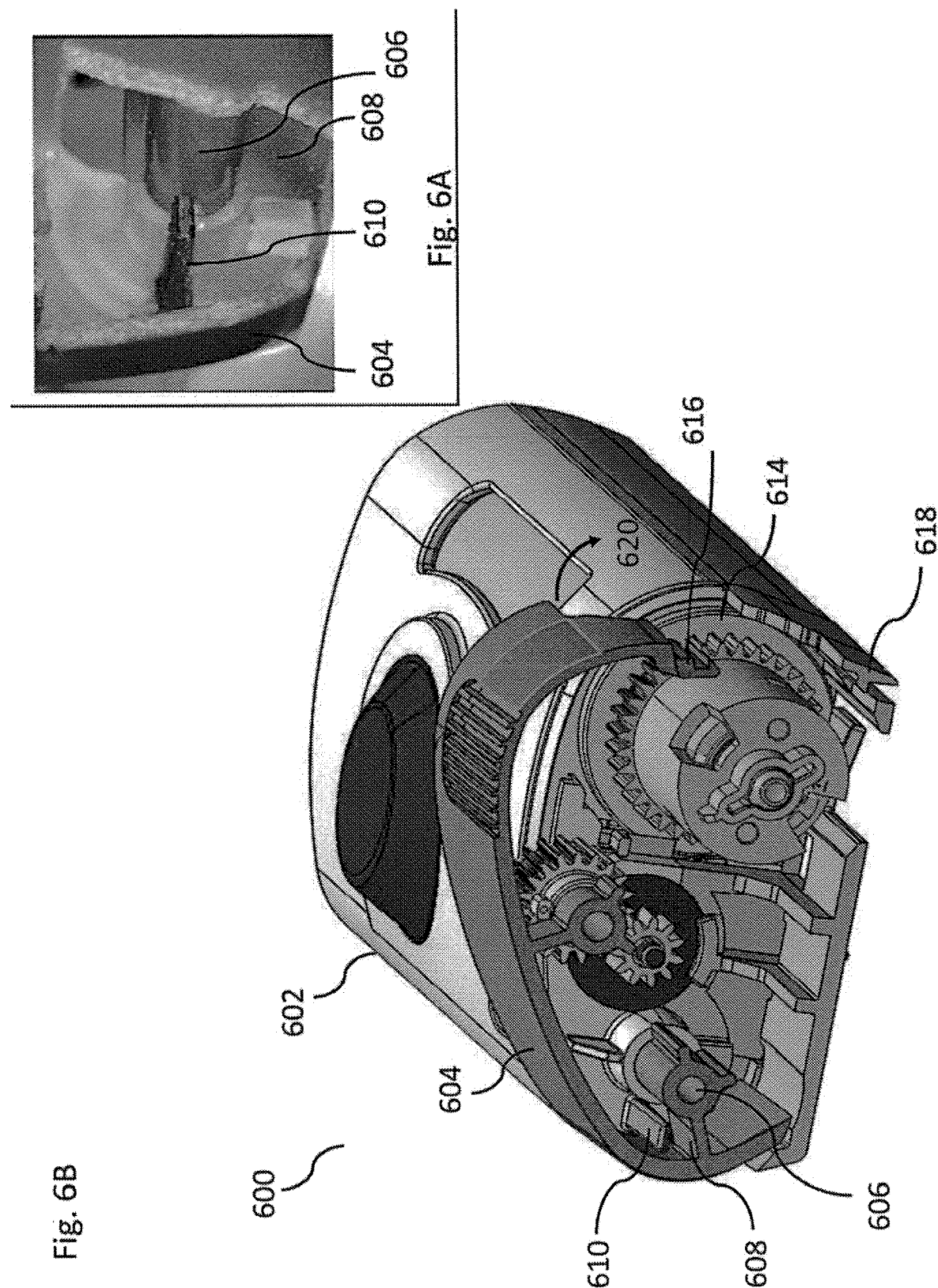

PARTIAL DOOR CLOSURE PREVENTION SPRING

CROSS-REFERENCE TO RELATED APPLICATIONS

This application is a section 371 of International Application No. PCT/US16/068049, filed Dec. 21, 2016, which was published Feb. 8, 2018 under International Publication No. WO 2018/026385 A1, which claims the benefit of U.S. Provisional Application No. 62/369,505, filed Aug. 1, 2016, the contents of which are incorporated herein by their entirety.

FIELD AND BACKGROUND OF THE INVENTION

The present invention, in some embodiments thereof, relates to a method for indicating the position of a door and, more particularly, but not exclusively, to a method for indicating the position of a medical device door.

SUMMARY OF THE INVENTION

Following are some examples of some embodiments of the invention:

Example 1. A drug delivery device, comprising: housing, wherein said housing defines an opening and a chamber for a drug cartridge;
a movable door connected to said housing, having a range of movement between a fully open position and a closed position, wherein said door blocks access to said opening when said door is in said closed position;
a biasing element connected to said housing or said door, wherein said biasing element is positioned to interfere with the movement of said door by applying an opening force to open said door when said range of movement of said door is near said closed position, thus defining an exclusion zone;
a locking mechanism between said door and said housing, said locking mechanism applies a locking force on said door greater and in an opposite direction to the force applied by said biasing element.

Example 2. The device of example 1, further comprising a drug dispensing mechanism; wherein closing of said movable door engages said drug dispensing mechanism to release drug from said drug cartridge.

Example 3. The device of examples 1 or 2, wherein said movable door is connected to said housing via a hinge, wherein said locking mechanism is positioned in a distance from said hinge at the contact point between said movable door and said housing.

Example 4. The device of any of the previous examples, wherein said movable door further comprising a hinge support, wherein when said movable door is closed said hinge support pushes said biasing element with a closing force which is greater than said opening force.

Example 5. The device of example 4, wherein when said opening force is greater than said closing force said biasing element moves said movable door to a perceptibly open position by pushing said hinge support.

Example 6. The device of example 4, wherein said movable door protrudes at least 4 mm from said housing when said movable door is in said perceptibly open position.

Example 7. The device of any of examples 3 to 6, wherein said biasing element applies said opening force when during the rotation of said movable door on said hinge said door reaches the last 20-30% of said range of movement.

Example 8. The device of any of examples 3 to 6, wherein said biasing element applies said opening force in the last 20-30 degrees of the rotation of said movable door on said hinge towards a closing position.

Example 9. The device of any one of examples 3 to 8, wherein said biasing element is positioned within said hinge.

Example 10. The device of any of the previous examples, wherein said door interlocks with locking geometries on said housing for locking said door.

Example 11. The device of any of the previous examples, wherein said locking mechanism irreversibly locks said movable door.

Example 12. The device of examples 1 or 2, wherein said door is a sliding door.

Example 13. The device of any of the previous examples, wherein said biasing element is a leaf spring, and/or a torsion spring.

Example 14. The device of any of the previous example, wherein said biasing element is a deformable element configured for elasticity deforming.

Example 15. The device of any of the previous examples, wherein said door further comprises a transmission to couple between a motor of said device and a drug cartridge when said door is in said closed position.

Example 16. A method for visually indicating that a door of a drug delivery device is open, comprising:
receiving by said door a closing force to move said door;
detecting that said door is not closed;
pushing said door with an opening force by a biasing element, to a perceptibly open position; and
indicating that said door is open by identifying said perceptibly open position of said door compared to said drug delivery device housing.

Example 17. The method of example 16, wherein said indicating further comprises indicating that said door is open by identifying at least one gap between said door and said drug delivery device housing.

Example 18. The method of examples 16 or 17, wherein said receiving further comprises receiving said closing force to move said door, wherein said closing force is greater than said opening force.

Example 19. The method of anyone of examples 16 to 18, wherein said detecting further comprises detecting that said door is not locked by a locking mechanism of said door and/or housing of said drug delivery device.

Example 20. The method of anyone of examples 16 to 19, wherein said indicating further comprises indicating that said door is open by visually identifying said perceptibly open position.

Example 21. The method of anyone of examples 16 to 19, wherein said indicating further comprises indicating that said door is open by touching said door and said drug delivery device housing.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-1C are schematic front views depicting different positions of a medical device door in relation to the medical device casing, according to some embodiments of the invention;

FIG. 2 is a graph showing the change in the force applied by a biasing element on a medical device door as a function of the door opening angle, according to some embodiments of the invention;

FIG. 3 is a flow chart depicting a process of closing a medical device door, according to some embodiments of the invention;

FIGS. 4A-4J are schematic views depicting the closing of a medical device rotating door, according to some embodiments of the invention;

FIGS. 5A-5G are schematic views depicting the closing of a medical device sliding door, according to some embodiments of the invention;

Figure 6C:
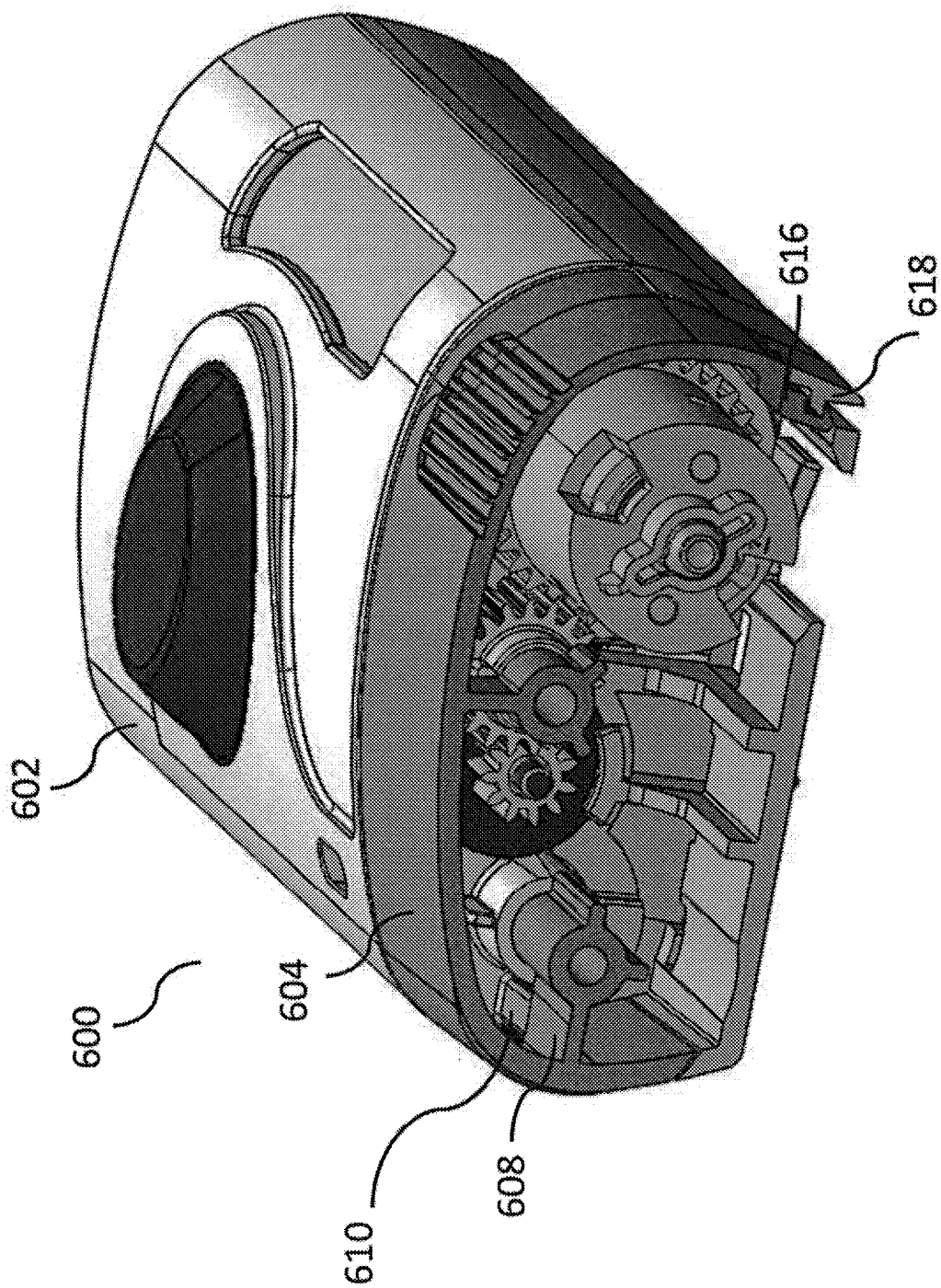
Figure 6D:
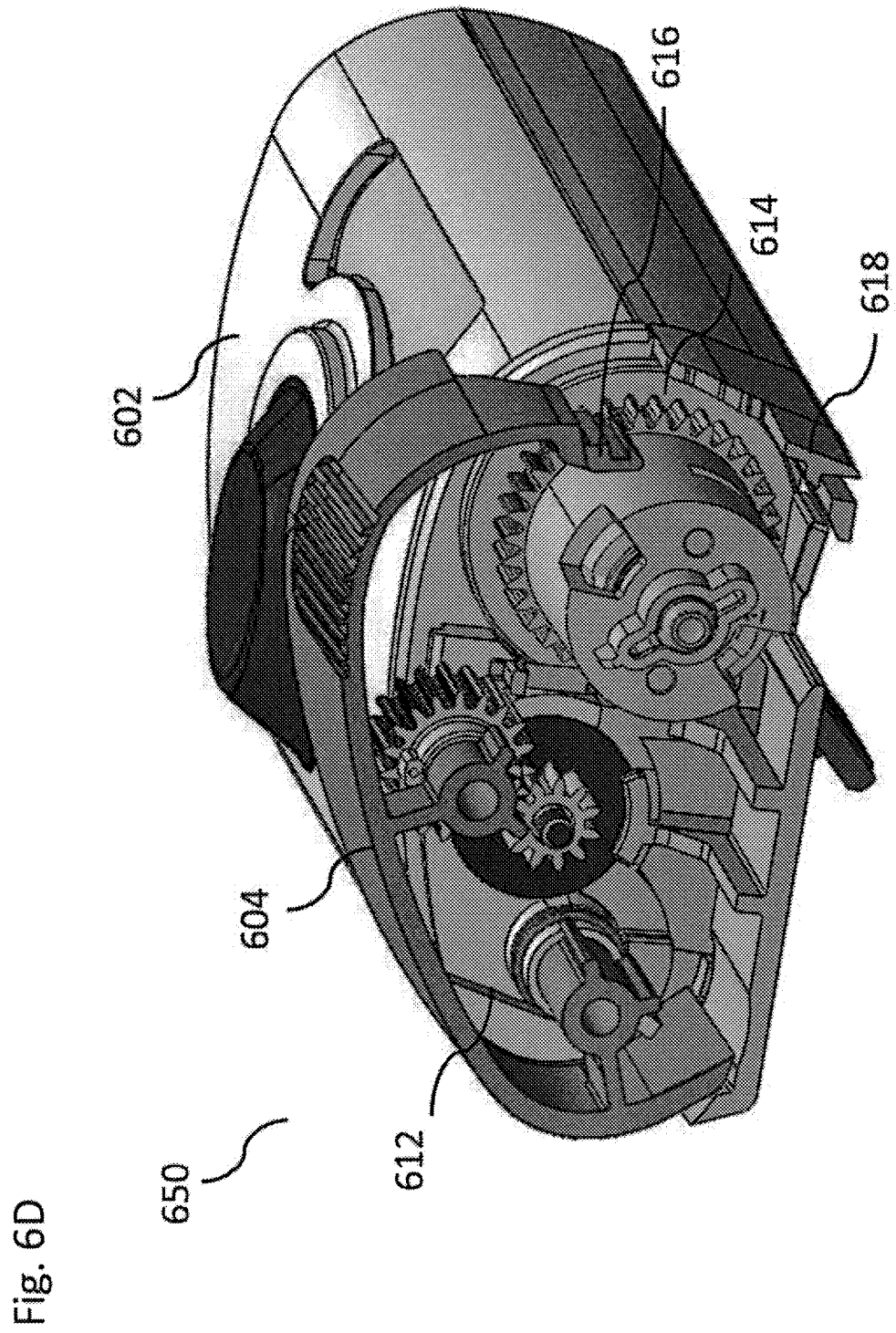
Figure 6E:
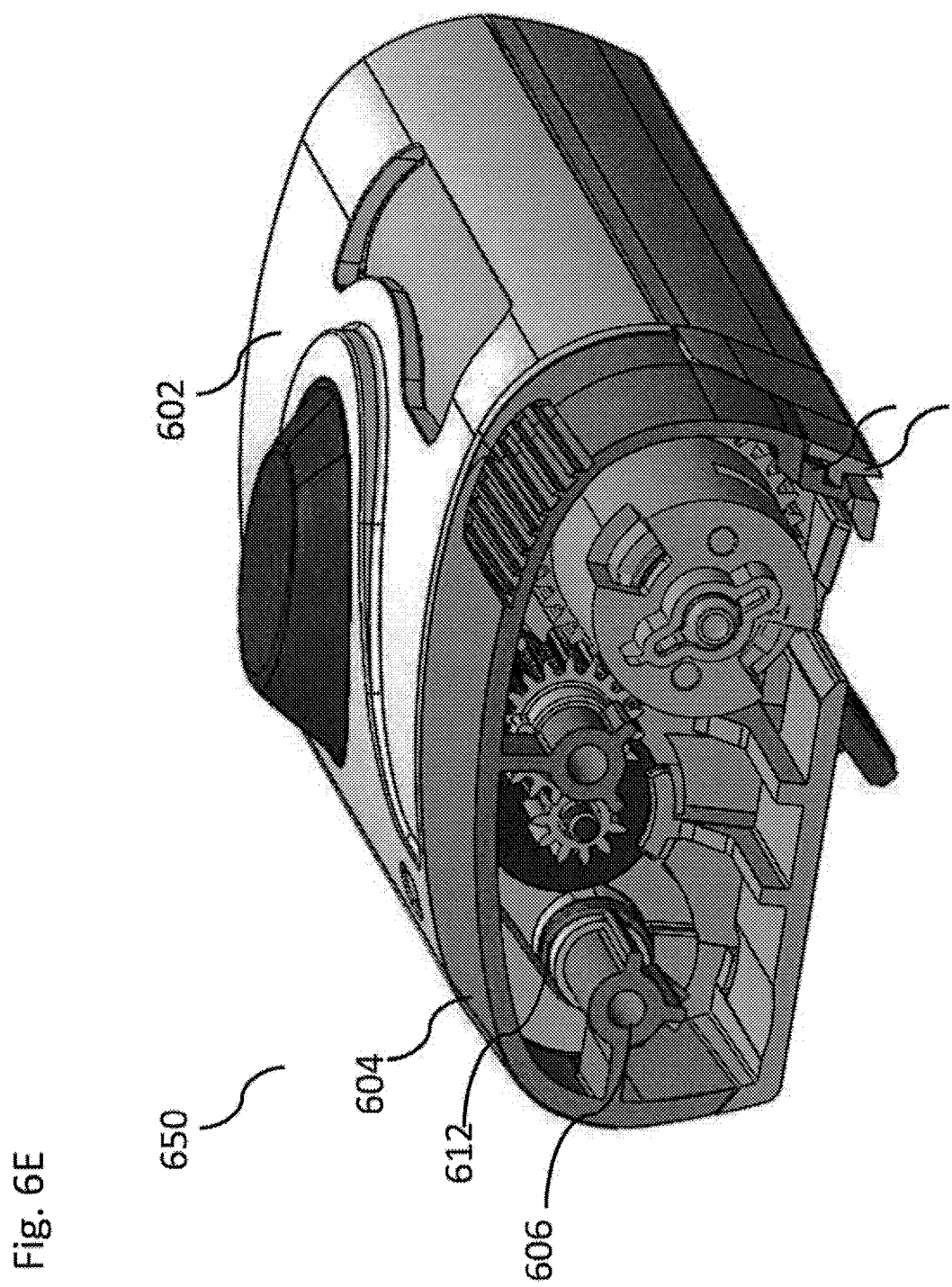
Figure 7A:
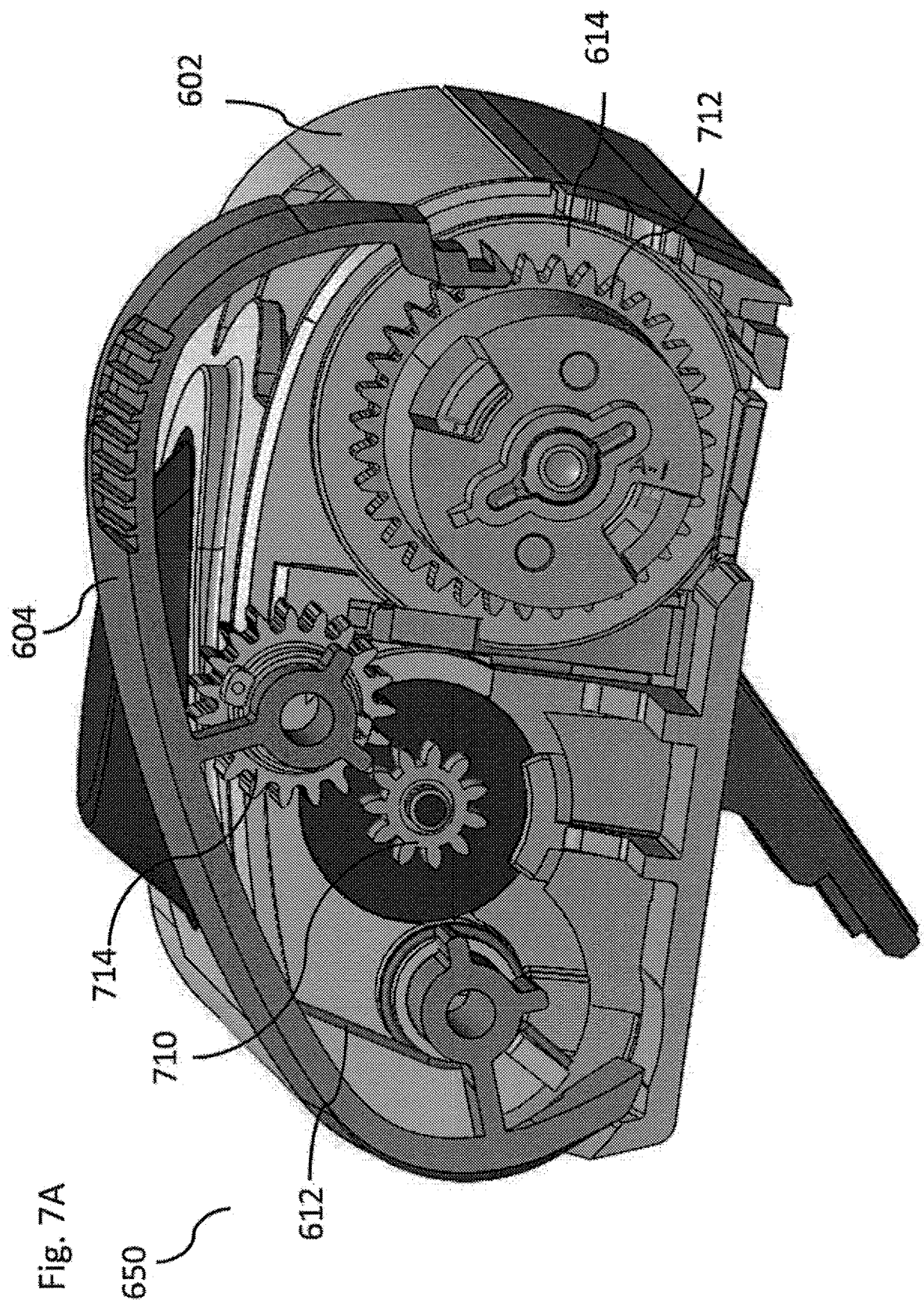
Figure 7B:
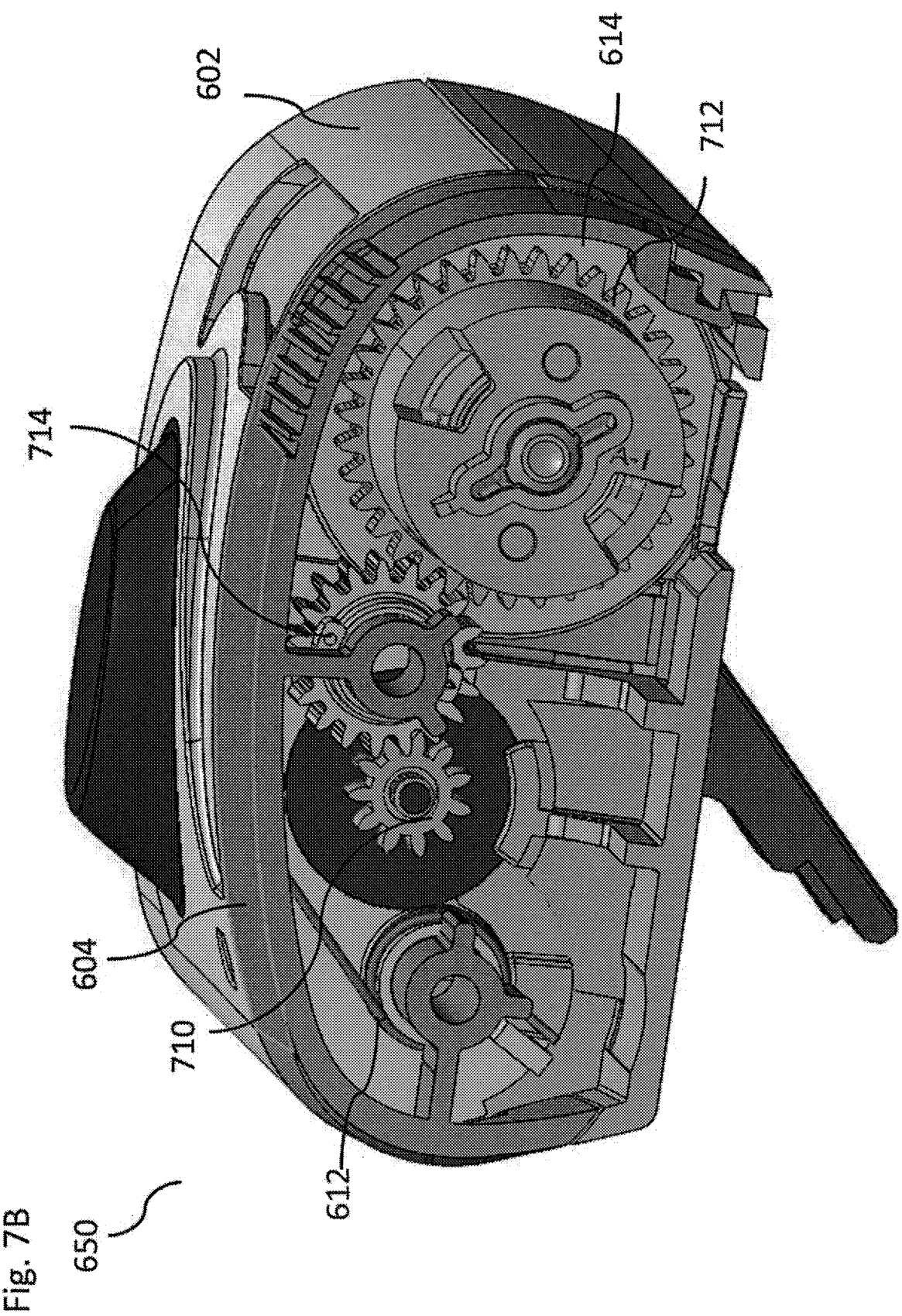

FIGS. 6A-6E are schematic views depicting different components of a medical device when the medical device door is in an open and a closed position, according to some embodiments of the invention; and FIGS. 7A-7B are schematic views of an engagement mechanism between a motor of a medical device and a cartridge inserted into the medical device when the door of the medical device is open and when the door is closed, according to some embodiments of the invention.

DESCRIPTION OF SPECIFIC EMBODIMENTS OF THE INVENTION

The present invention, in some embodiments thereof, relates to a method for indicating the position of a door and, more particularly, but not exclusively, to a method for indicating the position of a medical device door.

An aspect of some embodiments relates to preventing a medical device door from being in an exclusion zone. In some embodiments, the exclusion zone is located near the closing position of the door. Alternatively, the exclusion zone is located at the last 50% of the medical device door range of movement, for example the last 5, 10, 15, 20%. In some embodiments, the exclusion zone is located at the last 25 degrees, for example last 20, 15, 10 degrees of the rotation of the device door towards a closed position.

In some embodiments, a biasing element applies a force on the door, when the door is within the exclusion zone. In some embodiments, the biasing element pushes the door open to a perceptibly open position. In some embodiments, when the door is at a perceptibly open position, a user of the device receives a clear visual indication that the door is open. Alternatively, when the door is at a perceptibly open position, a user can feel by touching the door and/or the device that the door is open. In some embodiments, for example, when the door is at a perceptibly open position the door protrudes at least 2 mm, for example 3, 4, 5, 6, 7 mm, from the device casing. In some embodiments, a potential advantage of having a biasing element which generates a limited range exclusion zone is that the biasing element does not interfere with access into the device when it pushes the door wide open. Additionally, having a device with a door wide open, for example when the door significantly protrudes out from the casing, may lead to problems during packaging and/or transportation of the device.

In some embodiments, a user applies force on the door in an opposite direction to the force applied by the biasing element, for example to move the door to a closing position. In some embodiments, the force applied by the user is larger than the opening force applied by the biasing element. In some embodiments, if the door is not further pushed by a user, then the biasing element pushes the door to the perceptibly open position.

In some embodiments, when the door is pushed to a closed position, a closing mechanism located on the door and/or on the medical device applies a greater force compared to the force applied by the biasing element. In some embodiments, the locking mechanism can be released, for example to allow opening of the door to a perceptibly open position by the biasing element. Alternatively, the locking element prevents the re-opening of the door, for example to ensure that the door remains closed, for example in case of a single use device.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1A:
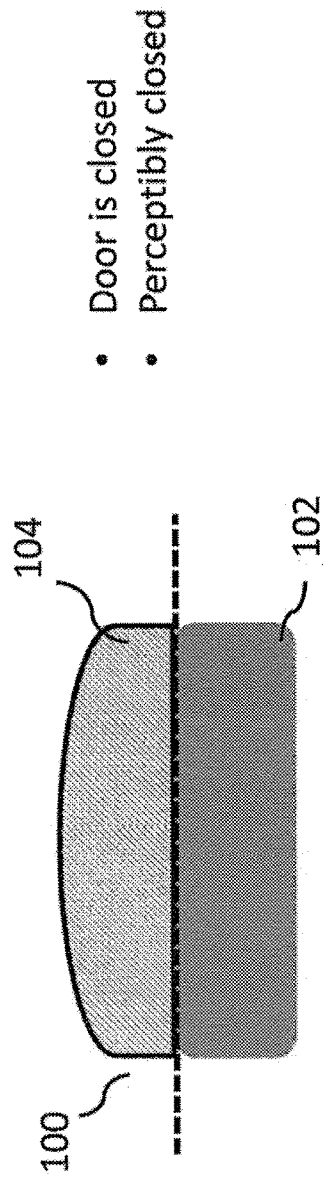
Figure 1B:
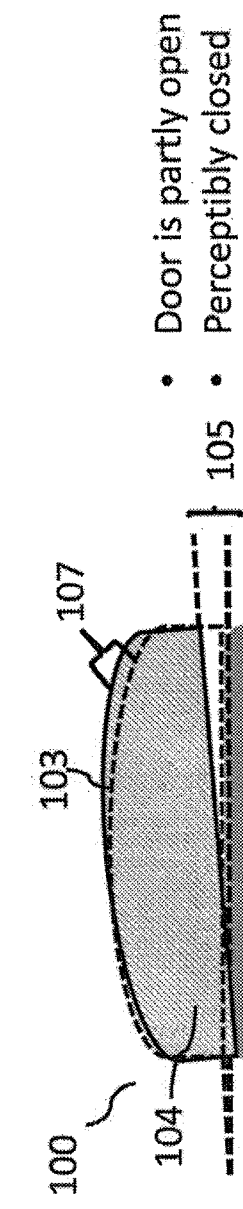
Figure 1C:
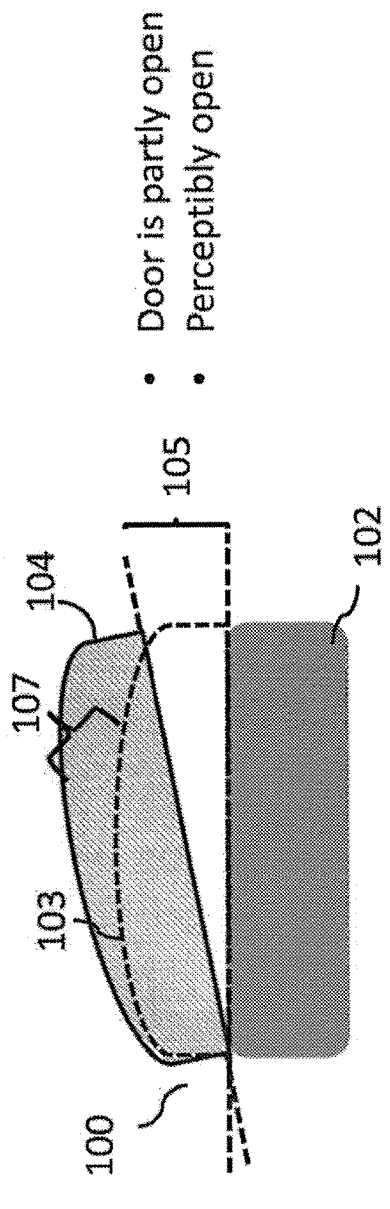

In some embodiments, a drug dispensing mechanism of a drug delivery device, for example medical device 100 in FIGS. 1A-1C, operates to dispense drug molecules only when the medical device door, for example door 104 is closed on the device housing 102, for example as shown in FIG. 1A. Optionally, when the door is closed, the door is locked by a locking mechanism. In some embodiments, when the door is fully closed, a user of the device receives a visual indication that the door is closed. In some embodiments, when the door is closed there are no visible gaps between the door and the housing. Additionally, the door and the housing form a uniform outer surface of the medical device.

In some embodiments, if the door is not closed or is in a nearly closed position, for example as shown in FIG. 1B the drug is not dispensed. In some embodiments, when the door is in a nearly closed position, a user receives a visual indication that the door is closed because, for example a gap 105 formed between the door 104 and the housing 102 is not wide enough to indicate that the door is still open, and therefore the door is perceptibly closed. In some embodiments, when the door is a nearly closed position, a gap 107 formed between the door and an upper part 103 of the housing is not visible, and cannot be identified by touching the outer surface of the medical device 100. In some embodiments, when the door is still open but is perceptibly closed, a user activates the device but a drug cannot be delivered.

In some embodiments, in order to indicate to a user that the door is not closed, the door 104 is placed in a perceptibly open position. In some embodiments, in a perceptibly open position the gap formed between the door 104 and the housing 102, for example gap 105 is wide enough to visually indicate and/or to be identified by touch that the door is not closed. In some embodiments, the gap 107 formed between the door 104 and the upper part 103 of housing 102 is also visible and can be identified by touching the outer surface of the medical device, for example the upper part of the medical device 100 In some embodiments, when a user receives the indication that the door is not closed, he can then apply more force to close the door and optionally to ensure locking of the door.

Exemplary Formation of an Exclusion Zone

According to some embodiments, in order to place the door in a perceptibly open position, an exclusion zone is formed. In some embodiments, the door is not allowed to be positioned within the exclusion zone, unless a user applies force on the door.

Figure 2:
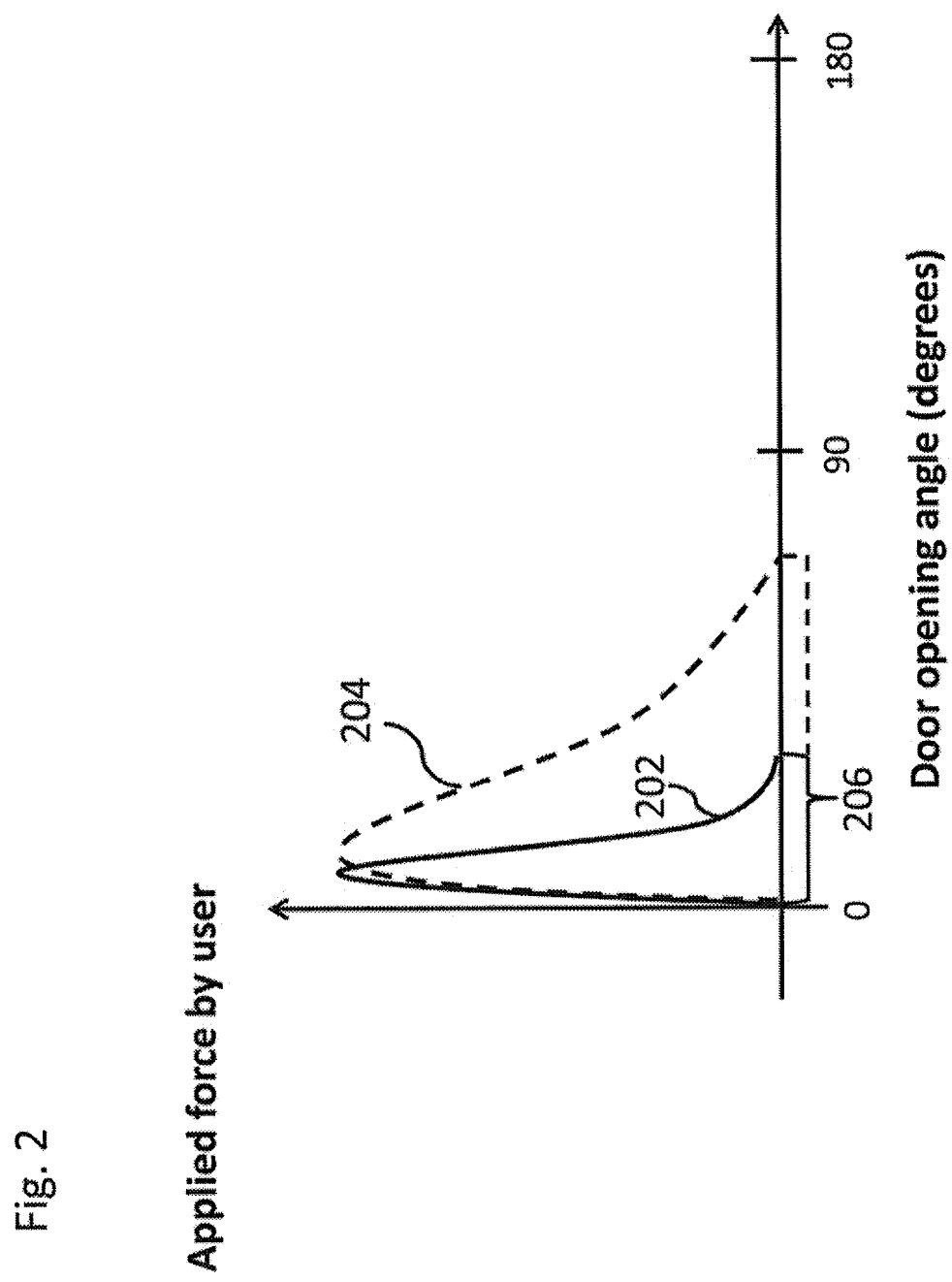

Reference is now made to FIG. 2, describing the formation of an exclusion zone for a door position, according to some embodiments of the invention.

According to some exemplary embodiments, a biasing element for example an elastic biasing element or a deformable biasing element applies force on the door when the door is reaching a closed position. In some embodiments, the biasing element continuously applies force on the door from a near closed position until the door reaches a closing position. In some embodiments, an exclusion zone as long as the biasing element applies force on the door. In some embodiments, the biasing element applies enough force to move the door to perceptibly open position if the total force applied on the door is in the direction of the force applied by the biasing element.

According to some exemplary embodiments, when the door is pushed from an open position to a closing position of 0 degrees between the door and the device housing, a biasing element starts to apply force on the door when the door opening degree is less than 90 degrees. In some embodiments, the biasing element applies force on the door until the door reaches an angle of 0 degrees. Optionally, the biasing element applies force on the door when the door is closed or locked.

According to some exemplary embodiments, when the door opening angle degree is less than 90 degrees, a biasing element, for example a torsion spring gradually applies force on the door. In some embodiments, for example as seen in graph 204 a user needs to apply force larger than the force applied by the torsion spring and in an opposite direction until the door is closed. In some embodiments, the increase in force applied by the user against the torsion spring is more gradual compared to the force that needs to be applied against a leaf spring as seen in graph 202. In some embodiments, the amount of force that needs to be applied by a user to close the door depends on the elasticity of the biasing element.

In some embodiments, the leaf spring starts to apply force on the door when the door angle is less than 45 degrees. In some embodiments, the leaf spring and the torsion spring form an exclusion zone 206, however the exclusion zone formed by the torsion spring is larger compared to the exclusion zone formed by the leaf spring. In some embodiments, force application in wider opening angles, for example by the torsion spring allows to form larger exclusion zones. In some embodiments, a larger exclusion zone allows for example, a better indication that the door of the medical device is open.

According to some exemplary embodiments, when the door is closed or reaches a near closing position, a locking mechanism locks the door. In some embodiments, the locking mechanism applies a force larger than the biasing element. In some embodiments, when the door is locked the force applied by the user to keep the door closed is zero, as shown in graphs 202 and 204.

Exemplary Process for Closing a Door

Figure 3:
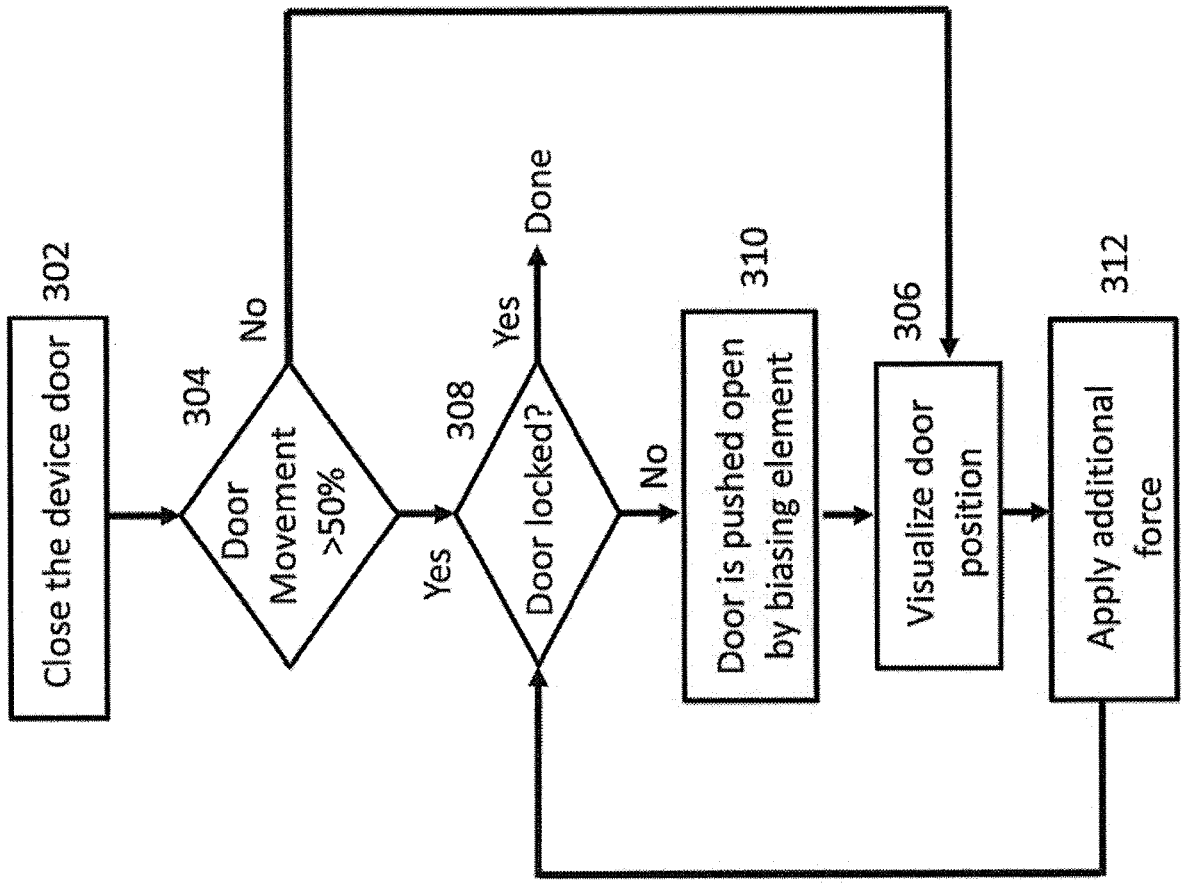

According to some exemplary embodiments, a medical device user, closes a door of the device to allow the device to operate according to a desired activation process. Reference is now made to FIG. 3, depicting a process for closing a door of a medical device, according to some embodiments of the invention.

According to some exemplary embodiments, the door is closed by a user of the medical device at 302. In some embodiments, the user closes the door by applying sufficient force on the door to allow the door movement to a closing position. In some embodiments, the force applied by the user is larger than the force applied by a biasing element. Additionally, the force applied by the user is in and in an opposite direction to the force applied by the biasing element. In some embodiments, the user applies force on the door, to move the door to a locking position According to some exemplary embodiments, the door movement is estimated at 304. In some embodiments, if the door moves less than 50% of the door range of movement, then the user visualizes the door position at 306, for example to receive a visual indication about the door position. In some embodiments, following the visualization of the door position, the user applies additional force to close the door at 312.

According to some exemplary embodiments, if the door moves more than 50% of the door range of movement, then the user checks whether the door is locked at 308. In some embodiments, if the door is locked, then no further actions are requires. Alternatively, if the door is not locked then a biasing element pushes the door open at 310. In some embodiments, the biasing element pushes the door to a perceptibly open position.

According to some exemplary embodiments, the user visualizes the door position at 306. In some embodiments, the user visualizes that the door is at a perceptibly open position at 306, optionally by visualizing a gap between the door and the device casing, for example gap 108 shown in FIG. 1C.

According to some exemplary embodiments, if the door is visualized in a perceptibly open position, then the user applies additional force to close the door at 312. In some embodiments, the user applies a larger force on the door at 312. In some embodiments, after the additional force is applied by the user, the door movement is estimated at 304, as previously described.

Exemplary Closing of a Rotating Door

Reference is now made to FIGS. 4A-4J depicting the closing of a rotating medical device door, according to some embodiments of the invention.

According to some exemplary embodiments, medical device 400 comprises a movable door, for example rotating door 404 and housing 402, and a biasing element 406 connected to housing 402. In some embodiments, the rotating door 404 is connected to housing 402 via a hinge 405 which allows the axial rotation of the rotating door 404. In some embodiments a hinge support 403 is connected to rotating door 404. In some embodiments, the biasing element is positioned on the left side of the hinge support. Alternatively, for example when the hinge is placed on the right side of the biasing element, the hinge support is positioned on the left side of the biasing element.

According to some exemplary embodiments, for example as shown in FIG. 4A, when the rotating door 404 is in an open position, biasing element 406 is not in contact with the door or with hinge support 403, and therefore does not apply force on the door.

According to some exemplary embodiments, for example as shown in FIG. 4B, biasing element 406 is in contact with the hinge support 403, and optionally applies minimal or zero force on hinge support 403. In some embodiments, in this position, the rotating door 404 is placed in a perceptibly open position, for example a position that allows a visual indication that the door is open. In some embodiments, the biasing element 406 makes contact with the rotating door 404 or with the hinge support 403 at the last 45 degrees 414, for example last 30, 25, 20, 15, 10 degrees of the door rotation towards closing position.

According to some exemplary embodiments, for example as shown in FIG. 4C, to close the rotating door, an additional force is applied in direction 410, in an opposite direction to the force applied by the biasing element 406 on the hinge support 403. In some embodiments, if the force applied in direction 410 is zero, or is smaller than the force applied by the biasing element 406, then the rotating door 404 is pushed open, for example to the perceptibly open position shown in FIG. 4B. Alternatively, if the force applied in direction 410 is larger than the force applied by the biasing element and is applied for a sufficient time period, the rotating door 404 is closed, for example as shown in FIG. 4D. In some embodiments, when the door is closed the hinge support pushes the biasing element into a groove within housing 402. Optionally, when the door is closed a locking mechanism locks the door. In some embodiments, the locking mechanism irreversibly locks the door.

Figure 4E:
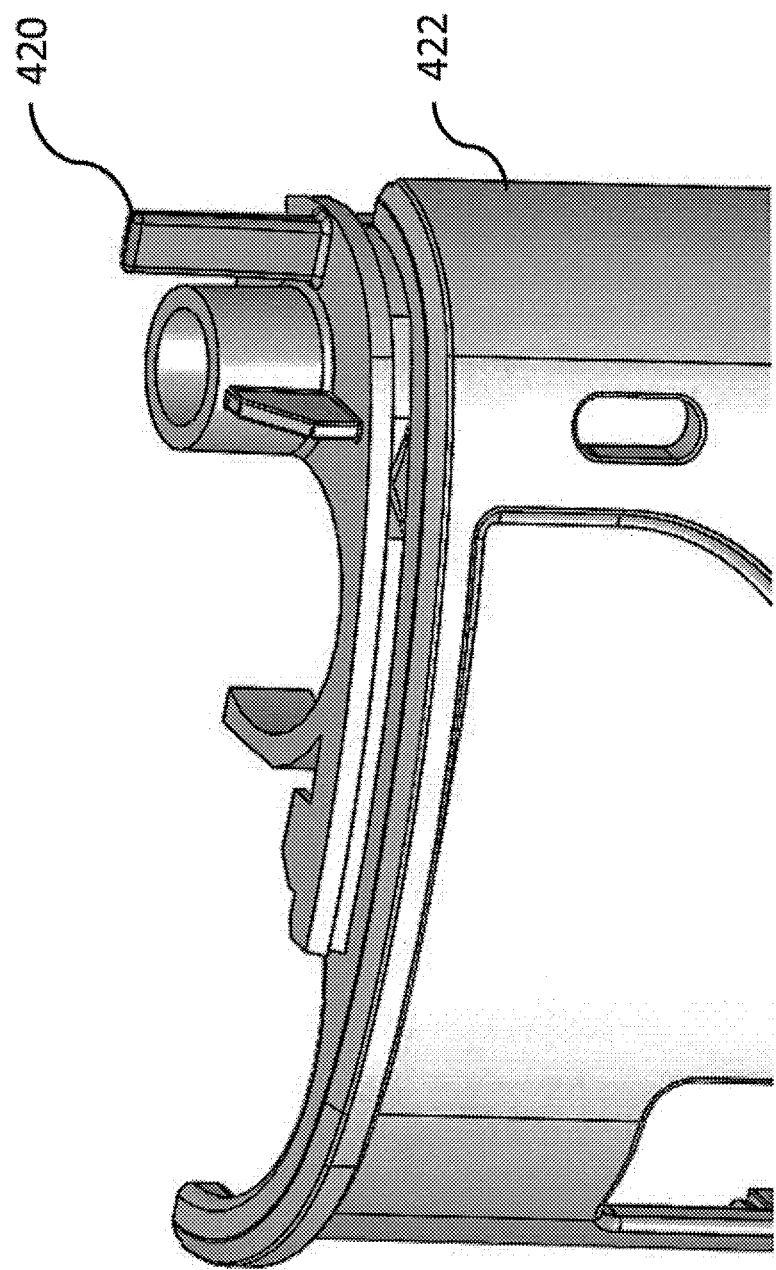

Reference is now made to FIGS. 4E-4G, depicting closing a rotating door by application of force against a biasing element in the form of a leaf spring, according to some embodiments of the invention.

According to some exemplary embodiments, for example as shown in FIG. 4E, a biasing element in the form of a leaf spring 420 is connected to housing 422. In some embodiments, when the door, for example door 424 is in perceptibly open position, leaf spring 420 is in contact with a hinge support 426 of door 424. In a perceptibly open position, the leaf spring 420 prevents the closure of door 424 unless an additional force is applied by moving the door 424 in direction 410. In some embodiments, when the door is moved in direction 410 until it reaches a closed position, the hinge support 426 applies sufficient force to bend leaf spring 420, for example as shown in FIG. 4G.

Figure 4H:
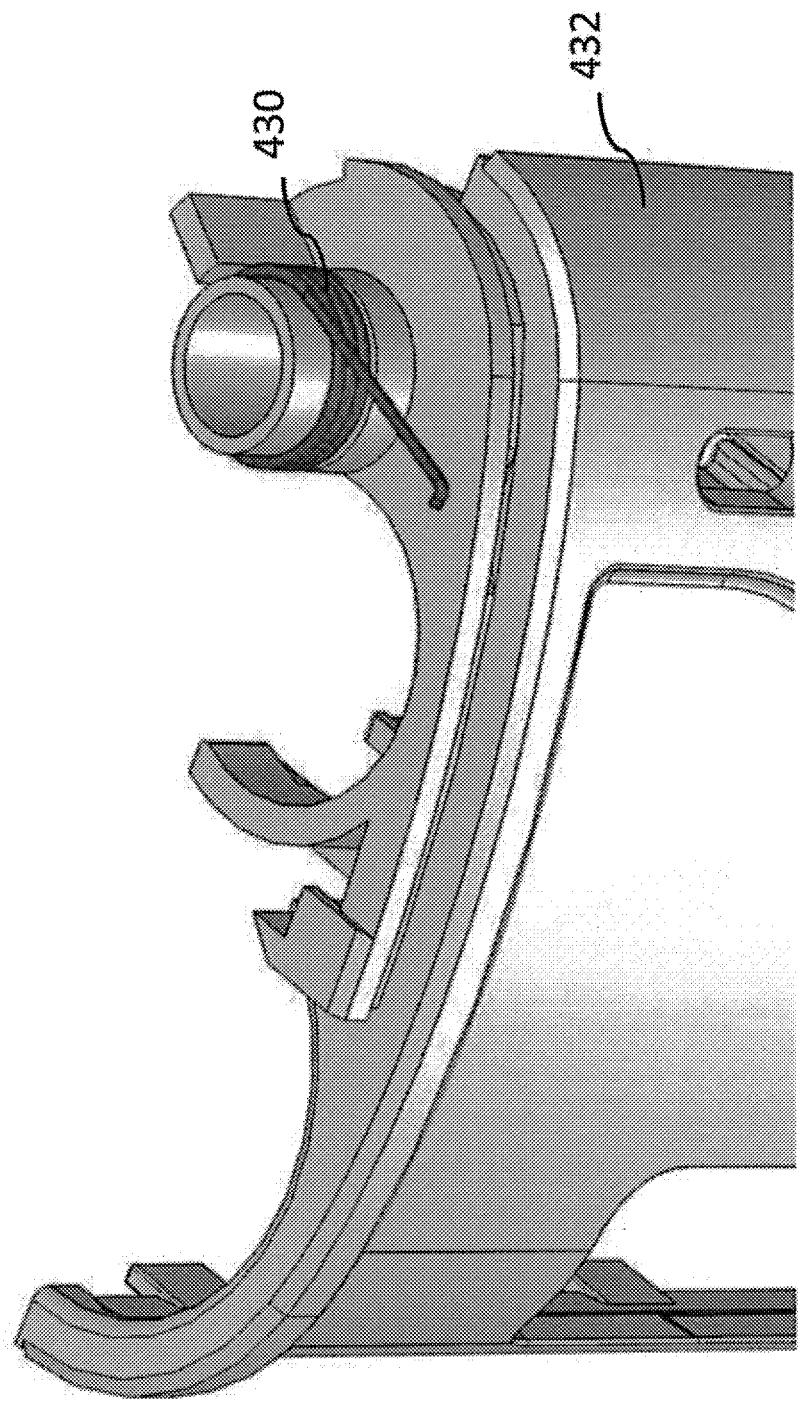

Reference is now made to FIGS. 4H-4J, depicting closing a rotating door by application of force against a biasing element in the form of a torsion spring, according to some embodiments of the invention.

According to some exemplary embodiments, for example as shown in FIG. 4H, a biasing element in the form of a torsion spring 430 is connected to housing 432. In some embodiments, when the door, for example door 434 is in perceptibly open position, torsion spring 430 is in contact with door 434. In a perceptibly open position, the torsion spring 430 prevents the closure of door 434 unless an additional force is applied by moving the door 434 in direction 410. In some embodiments, when the door is moved in direction 410 until it reaches a closed position, the door 434 applies sufficient force to bend torsion spring 430, for example as shown in FIG. 4J.

Exemplary Closing of a Sliding Door

Reference is now made to FIGS. 5A-5D depicting the closing of a sliding medical device door, according to some embodiments of the invention.

According to some exemplary embodiments, medical device 500 comprises a sliding door 502, housing 504 and a biasing element 506 connected to housing 504. In some embodiments, for example as shown in FIG. 5A, the sliding door 502 is open and is not in contact with the biasing element 506. In some embodiments, in this position device components are inserted into the housing 504, for example a drug cartridge.

Figure 5C:
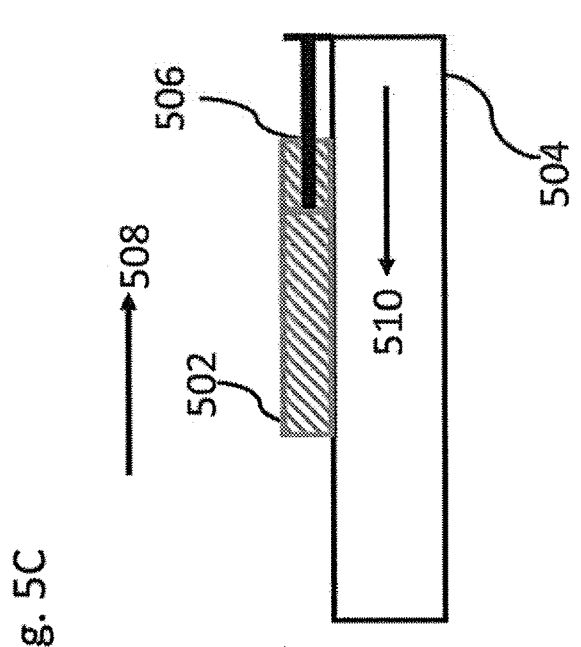
Figure 5D:
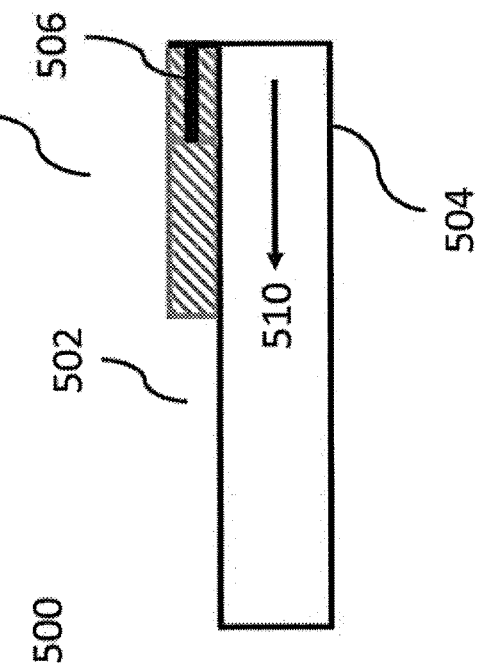
Figure 5A:
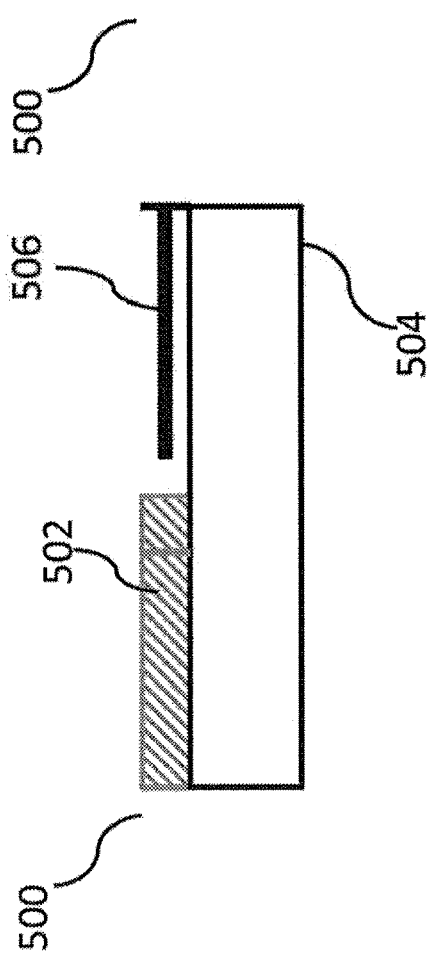
Figure 5B:
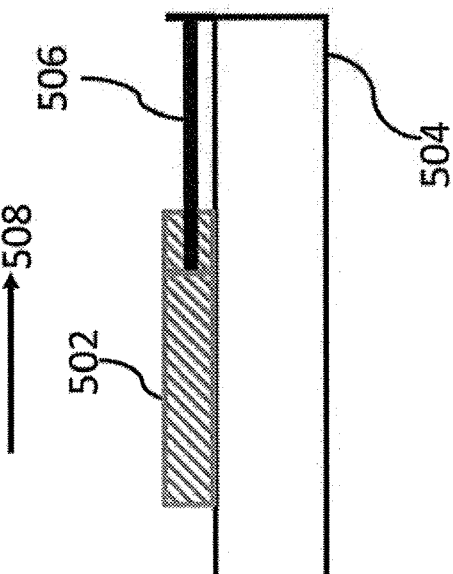

According to some exemplary embodiments, for example as shown in FIG. 5B a user applies force on the sliding door 502 in direction 508 to push the door to a closing position. In some embodiments, when the biasing element 506 applies minimal force or zero force on the sliding door 502, sliding door is positioned in a perceptibly open position.

According to some exemplary embodiments, in order to further push and close the sliding door 502, the user applies force in direction 508 in an opposite direction to the force applied by the biasing element, for example as shown in FIG. 5C. In some embodiments, the force applied by the user is larger than the force applied by the biasing element. Optionally, the user applies the force until the door is closed. In some embodiments, if the user stops applying the force before the sliding door 502 is closed, then the biasing element pushes the door in direction 510 to the perceptibly open position shown in FIG. 5B.

According to some exemplary embodiments, if the sliding door 502 is pushed by the user for a sufficient time period with a force larger than the force applied by biasing element, then the door is closed, for example as shown in FIG. 5D. In some embodiments, when the sliding door 502 is closed a locking mechanism placed on the door and/or on the housing 504 locks the door. In some embodiments, the locking mechanism applies force which is larger than the force applied by the biasing element, for example to prevent the opening of the door.

Figure 5G:
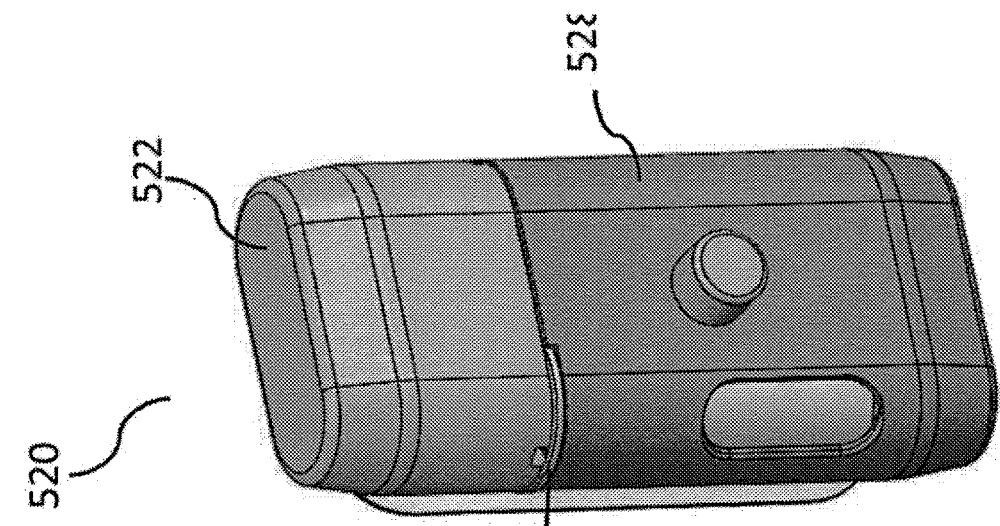
Figure 5F:
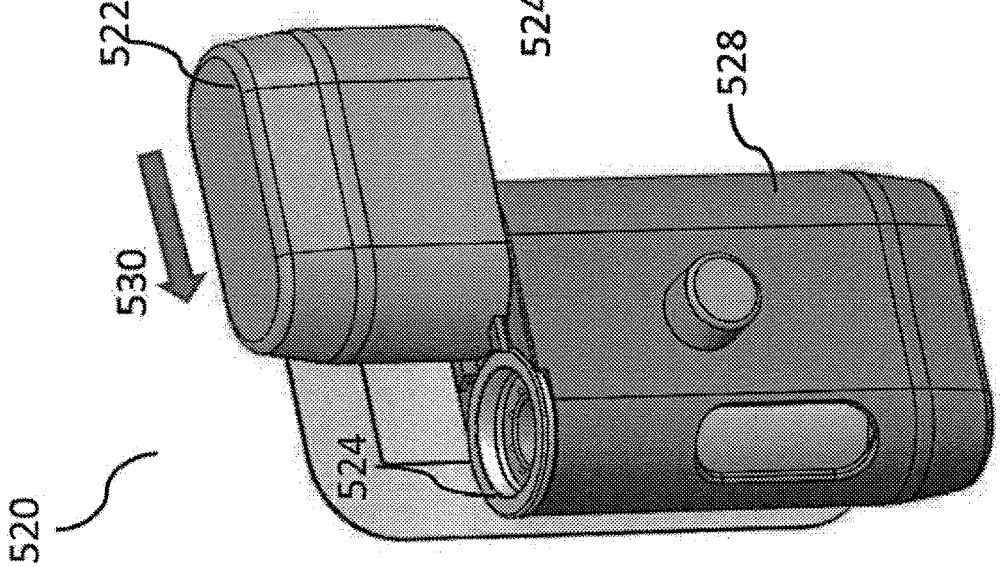
Figure 5E:
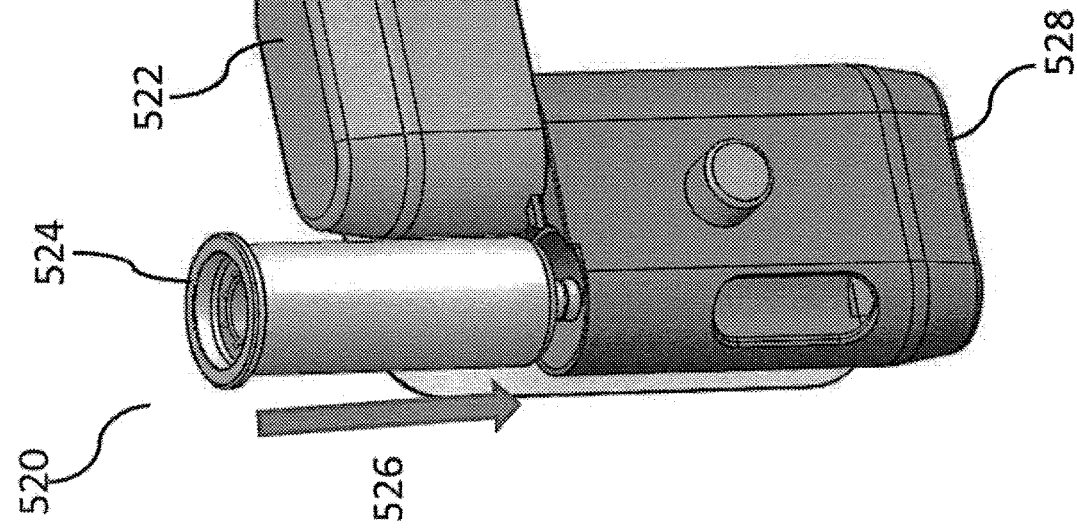

Reference is now made to FIGS. 5E-5G depicting a medical device with a sliding door in an open and a closed position, according to some embodiments of the invention.

According to some exemplary embodiments, when sliding door 522 of medical device 520 is in an open position, for example as shown in FIG. 5E, drug cartridge 524 is pushed in direction 526 into housing 528. In some embodiments, when the drug cartridge 524 is placed inside housing 528, the sliding door 522 is pushed in direction 530, for example to cover the drug cartridge 524. In some embodiments, to completely cover the drug cartridge sliding door 522 applies force against a biasing element connected to housing 528. In some embodiments, when the sliding door 522 is in a fully closed position, and is optionally locked, the drug cartridge 524 is fully covered, for example as shown in FIG. 5G. Optionally, when the sliding door 522 is locked, a drug can be delivered when medical device 520 is activated.

Exemplary Drug Delivery Device

Reference is now made to FIGS. 6A-6E depicting a drug delivery device, according to some embodiments of the invention.

According to some exemplary embodiments, a drug delivery device 600 comprising housing 602 and a movable door, for example rotating door 604 connected to housing 602 via hinge 606. In some embodiments, housing 602 defines a chamber for a drug reservoir, for example cartridge 614. In some embodiments, cartridge 614 stores drug molecules that are released when a drug dispensing mechanism of device 600 is engaged.

According to some exemplary embodiments, drug delivery device 600 further comprising a biasing element, for example a leaf spring 610 and/or torsion spring 612, connected to housing 602. In some embodiments, door 604 is connected to hinge 606 via hinge support 608. In some embodiments, when the door 604 is in a fully open position, for example as shown in FIG. 6A, the door is not in contact with the biasing element, and does not apply any force on the biasing element. In some embodiments, when the door 604 is pushed in direction 620 to a perceptibly open position, for example as shown in FIGS. 6B and 6D, the biasing element, for example leaf spring 610 or torsion spring 612 is in contact with the door 604. Alternatively, the biasing element is in contact with the hinge support 608. In some embodiments, when the door 604 is in a perceptibly open position, the biasing element prevents the closure of the door unless sufficient force is applied in direction 620.

According to some exemplary embodiments, when the door 604 moves in direction 620, the door applies additional force on the biasing element. Alternatively, when the door 604 moves in direction 620, the hinge support 608 applies additional force on the biasing element, for example on the leaf spring 610. Optionally, when the door moves in direction 620 an increasing force is applied on the biasing element.

According to some exemplary embodiments, door 604 is further pushed in direction 620 with a force greater than the force applied by the biasing element in order to reach a closing position. In some embodiments, when door 604 is closed, for example as shown in FIGS. 6C and 6E, a locking mechanism placed at the distal end of the door, for example locking mechanism 616 locks door 604 to housing 602. Alternatively or additionally, locking mechanism 618 placed on housing 602 locks door 602 and/or locking mechanism 616. In some embodiments, locking mechanism is placed in the contact point between door 604 and housing 602. Optionally, the locking mechanism is placed in a distance from hinge 606. In some embodiments, the door interlocks with locking geometries on said housing.

According to some exemplary embodiments, if door 604 is not locked and there is no force applied in direction 620, the biasing element, for example leaf spring 610 or torsion spring 612 pushes the door back to the perceptibly open position, for example the perceptibly open position shown in FIGS. 6B and 6D.

According to some exemplary embodiments, both a torsion spring and a leaf spring are connected to the housing of a medical device and apply force on the door. In some embodiments, the torsion spring applies force on the door at least at the last 50% of the door range of movement towards closure. In some embodiments, the leaf spring applies additional force on the door at least at the last 30% of the door range of movement towards closure.

According to some exemplary embodiments, when door 604 remains closed or locked, a drug dispensing mechanism of the drug delivery device is engaged, for example to allow drug dispensing from cartridge 614 upon device activation. In some embodiments, when door 604 is partially open, for example when door 604 is in a perceptibly open position, drug dispensing mechanism is not engaged and drug is not released from cartridge 614 when the device is activated.

According to some exemplary embodiments, the biasing element is an elastic element made from metal. Alternatively, the biasing element is a deformable element with a limited elastic range and is made, for example from plastic or elastomer.

Exemplary Engaging Drug Dispensing Mechanism

Reference is now made to FIGS. 7A and 7B, depicting the engagement of a drug dispensing mechanism, according to some embodiments of the invention.

According to some exemplary embodiments, medical device 650 comprising a motor mechanism 710 and a cartridge mechanism 712 of drug cartridge 614. In some embodiments, when door 604 is not closed for example when door is in a perceptibly open position the cartridge mechanism 712 is not engaged to motor mechanism 710. In some embodiments, when cartridge mechanism 712 is not engaged, a drug cannot be dispensed from cartridge 614, optionally even if the medical device 650 is activated by a user.

According to some exemplary embodiments, when door 604 is closed, for example by applying additional force against the biasing element 612, the cartridge mechanism 712 is engaged to motor mechanism 710. In some embodiments, a door transmission 714 is connected to door 604 and is coupled between the motor mechanism 710 and the cartridge mechanism 712, for example as shown in FIG. 7B. In some embodiments, when door 604 is closed, the door transmission 714 delivers the rotation of the motor mechanism 710 to the cartridge mechanism 712, for example to dispense drug from cartridge 614 upon medical device 650 activation.

It is expected that during the life of a patent maturing from this application many relevant biasing elements will be developed; the scope of the term biasing element is intended to include all such new technologies a priori.

As used herein with reference to quantity or value, the term "about" means "within ±10% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A drug delivery device, comprising:
   a housing defining an opening and a chamber configured to receive a drug cartridge;
   a motor within the housing;
   a door connected to the housing, the door having a range of movement between a fully open position and a closed position, wherein the door blocks access to the opening when the door is in the closed position;
   a transmission that is configured to couple the motor and the drug cartridge when the door is in the closed position and decouple the motor and the drug cartridge when the door is in the open position;
   a biasing element connected to the housing or the door, wherein the biasing element is positioned to interfere with the movement of the door by applying an opening force to open the door when the door reaches a last 30 degrees of a rotation of the door toward the closed position or when the door reaches a last 30% of the range of movement during the rotation of the door toward the closed position; and
   a locking mechanism between the door and the housing, the locking mechanism applying a locking force on the door greater and in an opposite direction to the opening force applied by the biasing element.

2. The drug delivery device of claim 1, further comprising a drug dispensing mechanism, wherein closing of the door engages the drug dispensing mechanism to release drug from the drug cartridge.

3. The drug delivery device of claim 1, wherein the door is connected to the housing via a hinge, and wherein the locking mechanism is at a contact point that is between the door and the housing and that is spaced from the hinge.

4. The drug delivery device of claim 1, wherein the door further comprises a hinge support, and wherein when the door is in the closed position, the hinge support pushes the biasing element with a closing force which is greater than the opening force.

5. The drug delivery device of claim 4, wherein when the opening force is greater than the closing force, the biasing element moves the door to an intermediate position by pushing the hinge support, the intermediate position being between the closed position and the fully open position.

6. The drug delivery device of claim 5, wherein the door protrudes at least 4 mm from the housing when the door is in the intermediate position.

7. The drug delivery device of claim 3, wherein the biasing element is positioned within the hinge.

8. The drug delivery device of claim 1, wherein the door interlocks with the housing for locking the door.

9. The drug delivery device of claim 1, wherein the locking mechanism irreversibly locks the door.

10. The drug delivery device of claim 1, wherein the door is a sliding door.

11. The drug delivery device of claim 1, wherein the biasing element is a leaf spring or a torsion spring.

12. The drug delivery device of claim 1, wherein the biasing element is configured to elasticity deform.

* * * * *